(12) United States Patent
Chang et al.

(10) Patent No.: US 11,007,234 B2
(45) Date of Patent: May 18, 2021

(54) ANAEROPLASMATALES FOR USE IN THE TREATMENT OR PREVENTION OF AN INFLAMMATORY DISORDER OF THE DIGESTIVE SYSTEM

(71) Applicant: Deutsches Rheuma-Forschungszentrum Berlin, Berlin (DE)

(72) Inventors: Hyun-Dong Chang, Berlin (DE); Alexander Beller, Berlin (DE); Andreas Radbruch, Berlin (DE)

(73) Assignee: DEUTSCHES RHEUMA-FORSCHUNGSZENTRUM BERLIN, Berlin (DE)

( * ) Notice: Subject to any disclaimer, the term of this patent is extended or adjusted under 35 U.S.C. 154(b) by 139 days.

(21) Appl. No.: 16/124,610

(22) Filed: Sep. 7, 2018

(65) Prior Publication Data
US 2019/0076487 A1 Mar. 14, 2019

(30) Foreign Application Priority Data

Sep. 8, 2017 (EP) .................... 17190070
Dec. 4, 2017 (EP) .................... 17205155

(51) Int. Cl.
| | |
|---|---|
| A61K 35/741 | (2015.01) |
| A61P 1/00 | (2006.01) |
| A23L 33/00 | (2016.01) |
| A61K 35/74 | (2015.01) |
| A61K 9/00 | (2006.01) |

(52) U.S. Cl.
CPC ............ *A61K 35/741* (2013.01); *A23L 33/00* (2016.08); *A61K 9/0053* (2013.01); *A61K 35/74* (2013.01); *A61P 1/00* (2018.01); *A61K 9/0056* (2013.01)

(58) Field of Classification Search
None
See application file for complete search history.

(56) References Cited

U.S. PATENT DOCUMENTS

2012/0269791 A1* 10/2012 Israelsen .............. A61K 35/744
424/93.45
2015/0093360 A1 4/2015 McKenzie et al.
2017/0246214 A1 8/2017 Sadowsky et al.

FOREIGN PATENT DOCUMENTS

WO WO-2012122478 A1 * 9/2012 ............... A61K 9/16

OTHER PUBLICATIONS

Knoll et al., "Gut microbiota differs between children with Inflammatory Bowel Disease and healthy siblings in taxonomic and functional composition: a metagenomic analysis", American Journal of Physiology Gastrointestinal and Liver Physiology, vol. 312, pp. G327-G339 (Year: 2017).*
Robinson et al., "Fecal Microbiota and Metabolome in a Mouse Model of Spontaneous Chronic Colitis: Relevance to Human Inflammatory Bowel Disease", Inflammatory Bowel Diseases, vol. 22, pp. 2767-2787 (Year: 2016).*
European Search Report in corresponding European Application No. EP 17 20 5155, dated Jun. 1, 2018.
Olbjorn et al. 2017 "Microbial characterization of pediatric inflammatory bowel disease and stratification into disease severity groups" *Gastroenterology*, Meeting Abstract, in 1 page.
Roediger & Macfarlane 2002 "A role for intestinal mycoplasmas in the aetiology of Crohn's disease?" *Journal of Applied Microbiology* 92: 377-381.

* cited by examiner

Primary Examiner — Michelle F. Paguio Frising
(74) Attorney, Agent, or Firm — Knobbe, Martens, Olson & Bear, LLP

(57) ABSTRACT

A composition including one or more bacteria of the order Anaeroplasmatales for use as a medicament in methods of treatment or prevention of an inflammatory disorder of the digestive system. Preferred embodiments of the invention relate to methods employing *Anaeroplasma* in the treatment or prevention of an inflammatory disorder of the digestive system. Preferably, the inflammatory disorders of the digestive system are inflammatory bowel disease, colitis, Crohn's disease (CD) or ulcerative colitis (UC). Furthermore, it is preferable that the composition of the present invention causes increased TGF-$\beta$ and/or IgA production in the intestine or other component of the digestive tract compared to subjects who have not received administration of the composition.

14 Claims, 9 Drawing Sheets

Specification includes a Sequence Listing.

A

B

C

SEQUENCE LISTING

<160> NUMBER OF SEQ ID NOS: 4

<210> SEQ ID NO 1
<211> LENGTH: 21
<212> TYPE: DNA
<213> ORGANISM: Mus musculus

<400> SEQUENCE: 1
cacagctcac ggcaccggag a                                              21

<210> SEQ ID NO 2
<211> LENGTH: 23
<212> TYPE: DNA
<213> ORGANISM: Mus musculus

<400> SEQUENCE: 2
gctgtactgt gtgtccaggc tcc                                            23

<210> SEQ ID NO 3
<211> LENGTH: 23
<212> TYPE: DNA
<213> ORGANISM: Mus musculus

<400> SEQUENCE: 3
cgaggtcaca ggagaaggga cgc                                            23

<210> SEQ ID NO 4
<211> LENGTH: 22
<212> TYPE: DNA
<213> ORGANISM: Mus musculus

<400> SEQUENCE: 4
ccgaaagagt ctctgcagct cc                                             22

ANAEROPLASMATALES FOR USE IN THE TREATMENT OR PREVENTION OF AN INFLAMMATORY DISORDER OF THE DIGESTIVE SYSTEM

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 28996000_1.txt, the date of creation of the ASCII text file is Sep. 7, 2018, and the size of the ASCII text file is approximately 1.0 KB. The information in the electronic format of the Sequence Listing is incorporated herein by reference in its entirety.

FIELD

The invention relates to a composition comprising one or more bacteria of the order Anaeroplasmatales for use as a medicament in methods of treatment or prevention of an inflammatory disorder of the digestive system. Preferred embodiments of the invention relate to methods employing *Anaeroplasma* in the treatment or prevention of an inflammatory disorder of the digestive system. Preferably, the inflammatory disorders of the digestive system are inflammatory bowel disease, colitis, Crohn's disease (CD) or ulcerative colitis (UC). Furthermore, it is preferable that the composition of the present invention causes increased TGF-β and/or IgA production in the intestine or other component of the digestive tract compared to subjects who have not received administration of the composition.

BACKGROUND

IgA is an essential component of the mucosal barrier, protecting it from colitogenic bacteria (1), which are known to cause inflammation of the digestive tract. The production of intestinal IgA as such is controlled by microbiota, as germ-free mice have little intestinal IgA unless they are repopulated with microbiota (2, 3). So far, it has not been clear which bacteria direct production of IgA, as opposed to immunoglobulins of other isotypes, and which cellular and molecular mechanisms are responsible for this. Class switching to IgA occurs predominantly in B lymphocytes in Peyer's patches (PP) (4), and is dependent on T follicular helper (Tfh) cells expressing TGF-beta (5, 6). TGF-beta induces IgA switch transcripts (7, 8), an essential prerequisite for IgA antibody class switch recombination (9).

Inflammatory bowel disease (IBD) is a group of inflammatory conditions of the colon and small intestine. Crohn's disease (CD) and/or ulcerative colitis (UC) represent the two most important inflammatory bowel diseases (IBD). They are characterized by chronic, relapsing tissue-destroying inflammatory processes in the digestive system. To date, etiology and pathogenesis of CD as well as UC are unclear. While inflammation in UC predominantly appears in the mucosa and submucosa of colon and rectum, CD is characterized by wall-penetrating, granulomatous inflammatory processes of the entire gastrointestinal tract. It is thought that colitogenic bacteria are involved in the pathogenesis of inflammatory disorders of the digestive system, such as inflammatory bowel disease and specifically Crohn's disease (CD) and/or ulcerative colitis (UC). However, no effective therapies for inflammatory disorders of the digestive system are available. Therefore, new therapies are urgently needed.

Olbjørn et al. ("*Microbial Characterization of Pediatric Inflammatory Bowel Disease and Stratification into Disease Severity Groups*", Gastroenterology, W.B. Saunders Co, US; 22 Apr. 2017) have reported that the microbiota profiles of pediatric IBD patients differ significantly from the profiles of non-IBD patients.

In the context of developing new therapeutic approaches for colitis, it has been suggested in US 2017/246214 A1 to use compositions comprising bacteria of the gastrointestinal tract, such as bacteria of the phylum Tenericutes. Similarly, US 2015/093360 A1 describes the treatment of gastrointestinal diseases by administering therapeutic compositions containing non-pathogenic, germination-competent bacterial spores obtained from fecal material, wherein the compositions may contain bacterial spores of the class Mollicutes. However, the relevant prior art refers to a great variety of bacteria that may be used for the treatment of colitis without differentiating between the specific effects and benefits of the individual phyla, classes, orders, families, genera or species of bacteria that may be used.

On the other hand, Roediger et al. (*A role for intestinal mycoplasmas in the aetiology of Crohn's disease?*", Journal of applied microbiology, 1 Jan. 2002, pages 377-381) suggest a role of *Mycoplasma* in the aetiology of Crohn's disease without providing clear evidence for this hypothesis. This disclosure suggests that arguments exist against a positive effect of *Mycoplasma* in the treatment of gastrointestinal inflammatory disorders.

SUMMARY

In light of the prior art the technical problem underlying the present invention is to provide alternative and/or improved means for the treatment of inflammatory disorders of the digestive system. This problem is solved by the features of the independent claims. Preferred embodiments of the present invention are provided by the dependent claims.

The invention therefore relates to a composition comprising one or more bacteria of the order Anaeroplasmatales for use as a medicament in the treatment or prevention of an inflammatory disorder of the digestive system.

Furthermore, the invention relates to a method for treating or preventing an inflammatory disorder of the digestive system in a subject, wherein the method comprises administering a composition comprising one or more bacteria of the order Anaeroplasmatales to the subject. The present invention is based on the entirely surprising finding that bacteria of the order Anaeroplasmatales induce higher levels of IgA in the digestive system of a subject. Subjects whose intestinal microbiota composition comprise bacteria of the order Anaeroplasmatales display elevated levels of IgA in the feces and in the lumen of the organs of the gastrointestinal tract as compared to subjects whose intestinal microbiota does not comprise bacteria of the order Anaeroplasmatales.

Immunoglobulin A (IgA) is the predominant class of antibodies produced in intestinal immune responses, and protecting from colitogenic bacteria. Colitogenic bacteria are thought to be one of or even the major cause of inflammatory disorder of the digestive system, especially IBD, CD and UC. It has been shown that colitogenic bacteria can be attacked by the gastrointestinal immune system through IgA-mediated immune-responses and that IgA is an essential component of the mucosal barrier, protecting it from colitogenic bacteria. However, in cases when an inflammatory disorder of the digestive system has been established the gastrointestinal immune system may have failed to control the colitogenic bacteria through production of specific IgA, which might be due to a generally decreased level of IgA in the gastrointestinal tract. This generally decreased IgA-level may lead to a much decreased ability to control or fight expansion and/or establishment of colitogenic bacteria. This may be associated with penetration of the mucosal barrier by colitogenic bacteria, leading to more severe inflammation of the gastrointestinal system.

IgA expression as such is not an intrinsic property of the mucosal immune system, but rather is induced by the microbiota. However, it has remained unclear, which bacteria and how they control mucosal IgA production. In the context of the present invention, it was surprisingly found that bacteria of the order Anaeroplasmatales induce production if IgA in the gastrointestinal system, which leads to elevated levels of IgA.

In preferred embodiments, the invention relates to one or more bacteria of the order Anaeroplasmatales that induce production of IgA in the gastrointestinal system. Preferably, the one or more bacteria of the composition of the present invention cause IgA production in the intestine or other component of the digestive tract. A preferred bacterium of the order Anaeroplasmatales causing IgA production in the gastrointestinal system is *Anaeroplasma*. It is a great advantage of the present invention, that bacteria of the order Anaeroplasmatales selectively induce IgA expressing germinal center B cells in Peyer's patches and IgA secreting plasma cells in the lamina propria of the small intestine, resulting in significantly increased mucosal IgA, while the numbers of germinal center B cells expressing IgG1 and other antibody classes in Peyer's patches appear to not be affected by the presence of absence of bacteria of the order Anaeroplasmatales. Therefore, bacteria of the order Anaeroplasmatales do not induce an imbalance in the gastrointestinal immune system at the cost of other immunoglobulin-classes, but rather selectively strengthen immune responses that are mediated by IgA.

In preferred embodiments, the invention relates to one or more bacteria of the order Anaeroplasmatales that do not induce an imbalance in the gastrointestinal immune system at the cost of other immunoglobulin-classes, but rather selectively strengthen immune responses that are mediated by IgA.

It is a further advantage that bacteria of the order Anaeroplasmatales induce the production of IgA by induction of expression of the IgA class switch-inducing cytokine TGF-beta in intestinal T follicular helper cells in the germinal centers of the gastrointestinal tract, which are mainly located in Peyer's patches (PP), which is the physiological pathway and mechanism leading to the induction of IgA production and IgA-mediated immune responses in the intestine. This is a great advantage, since it can be concluded that bacteria of the order Anaeroplasmatales, such as in particular *Anaeroplasma*, induce IgA production and an mucosal immune responses through the physiological mechanism of inducing TGF-beta in T follicular helper cells, while no pathogenic or artificial mechanisms or pathways are employed.

In preferred embodiments, the invention relates to one or more bacteria of the order Anaeroplasmatales that induce TGF-beta in T follicular helper cells. Preferably, the one or more bacteria of the composition of the present invention cause increased TGF-beta production in the intestine or other component of the digestive tract. A preferred bacterium of the order Anaeroplasmatales causing TGF-beta productin in the gastrointestinal system is *Anaeroplasma*.

A further surprising advantage of the present invention is that bacteria of the order Anaeroplasmatales can be transferred to subjects whose gastrointestinal microbiota do not comprise bacteria of the order Anaeroplasmatales. After transfer to such subjects, which have comparably low levels of gastrointestinal IgA, the level of IgA is rising substantially. This shows that bacteria of the order Anaeroplasmatales have a dominant effect with respect to IgA production and it is possible to establish bacteria of the order Anaeroplasmatales as part of the gastrointestinal microbiota of subjects who initially did not carry bacteria of the order Anaeroplasmatales in their microbiome upon administration of the Anaeroplasmatales to the gastrointestinal tract. Administration can occur orally, but also by any other suitable means known to the skilled person, such as oral gavage, endoscopic delivery, direct injection, or rectal administration.

Moreover, it was shown that bacteria of the order Anaeroplasmatales induced T follicular helper cells in the PP to induce TGF-beta, while expression of other genes and especially immune-response modulating cytokines was not modified by the presence of bacteria of the order Anaeroplasmatales in the gastrointestinal microbiota. Therefore, there may be no general shift or modification of the immune response by bacteria of the order Anaeroplasmatales but rather a specific and selective activation of IgA-mediated immune responses, which protect from colitogenic bacteria and therefore inflammatory diseases of the digestive system, while other branches of the immune system remain unaffected and can maintain their physiological function.

In preferred embodiments, the invention relates to one or more bacteria of the order Anaeroplasmatales that induce T follicular helper cells in the PP to induce TGF-beta without modifying expression of other genes and especially immune-response modulating cytokines. It is a further advantage of the present invention that bacteria of the order Anaeroplasmatales can induce the production of IgA irrespective of the specificity of the IgA producing B cells. In other words, the increase in IgA-levels may not be due to an increase of IgA specific for bacteria of the order Anaeroplasmatales but instead activate B cells and plasma cells of the gastrointestinal tract in general and irrespective of their specificity to develop into IgA-producing cells. Bacteria of the order Anaeroplasmatales may not target IgA responses to distinct bacteria, but rather direct IgA class switching as such. This is particularly beneficial for the treatment of diverse inflammatory diseases of the digestive system since such diseases can be caused by multiple different types of bacteria, which will all be controlled by generally increased levels of IgA.

In preferred embodiments, the invention relates to one or more bacteria of the order Anaeroplasmatales that induce the production of IgA irrespective of the specificity of the IgA producing B cells.

Bacteria of the order Anaeroplasmatales therefore qualify as a key anti-inflammatory component of the microbiota, since both, TGF-beta and IgA have been shown to protect from intestinal inflammation. This is particularly beneficial, since bacteria of the order Anaeroplasmatales therefore are even beneficial in inflammatory diseases of the digestive system that are not associated with colitogenic bacteria but only a deregulation and in particular activation of the inflammatory system.

The fact that bacteria of the order Anaeroplasmatales do not have a cell wall and thus can escape the recognition of cell wall-detecting immune receptors, such as innate immune receptors as for example Toll-like receptors (TLRs)

and NOD-like receptors (NLRs), is beneficial since this does not lead to a further induction of inflammation through such receptors, which might be detrimental in the context of an inflammatory disease.

The advantages of the present invention disclosed herein are particularly pronounced for embodiments of the invention, wherein the one or more bacteria of the order Anaeroplasmatales is *Anaeroplasma*.

Preferably, the one or more bacteria of the order Anaeroplasmatales is an anaerobic *mycoplasma*.

In particularly preferred embodiments of the present invention, the composition comprises *Anaeroplasma*.

The use of *Anaeroplasma* in the context of the present invention is particularly advantageous since it is very robust, as demonstrated by the fact that it survives in feces. Due to this robustness, it can be used in multiple formulations and compositions that can be stored over extended periods even at room temperature without losing activity/viability.

In a preferred embodiment the composition of the present invention is used in the treatment of prevention of colitis. Colitis is a disorder of the digestive system that can be associated with colitogenic bacteria, but may also be due to an overreaction of the inflammatory system of the gastrointestinal tract. It is particularly advantageous, that irrespective of the underlying pathological mechanism the composition of the present invention can be used to target both pathways, the immune response to colitogenic bacteria and dampening the inflammatory reaction.

It is especially preferred that the composition of the present invention is used for the treatment of prevention of inflammatory disorders of the digestive system that are associated with colitogenic bacteria. As explained above, bacteria of the order Anaeroplasmatales and in particular *Anaeroplasma* lead to an induction of IgA production in the gastrointestinal tract, which may be mediated through the induction of class-switching to IgA in B cells after TGF-beta stimulation. It has been described that colitogenic bacteria can be controlled and under pathological conditions reduced by IgA-mediated immune response. Accordingly, it is a great advantage that such immune responses can be enhanced through the administration of bacteria of the order Anaeroplasmatales to the gastrointestinal tract.

In further preferred embodiments of the invention the composition is used for the treatment of prevention of inflammatory disorders of the digestive system, which are associated with decreased levels of IgA in the gastrointestinal tract. Preferably, in the context of the inflammatory disorders of the digestive system of the present invention it is beneficial to induce IgA production in the gastrointestinal tract, for example by increasing the level of TGF-beta.

In a further embodiment of the present invention the inflammatory disorder of the digestive system is inflammatory bowel disease. Preferably, the inflammatory disorder of the digestive system is Crohn's disease (CD) or ulcerative colitis (UC).

It was particularly surprising that the administration of the composition of the present invention to individuals suffering from CD and UC is beneficial for the reduction symptoms and dampening pathogenic processes in all parts of the gastrointestinal tract that are affected, including the mouth, esophagus and gut, which are not or not excessively colonized by the intestinal microbiota, as well as in extra-intestinal sites that are affected.

It is especially preferred that the composition of the invention is in a form suitable for oral administration. Oral administration of the composition is associated with many advantageous, such as easy administration in form of a liquid or tablet or capsule that does not require assistance of medical personnel. Furthermore, administration does not require a health-institutional setting, but can be done at home or during travel. Furthermore, oral administration is not associated with any painful procedures and is usually associated with good compliance of the patient or subject to be treated.

Preferably, the composition of the present invention is prepared as a probiotic for oral administration suitable as a dietary supplement. Preferably, the composition is administered regularly, for example once daily in form of a food supplement or food that can be consumed with a meal, to subjects for the prevention of inflammatory disorders of the digestive system as a prophylactic measure. This might lead to a establishment of a beneficial intestinal microbiome comprising a suitable percentage of bacteria of the order Anaeroplasmatales to establish an anti-inflammatory milieu with high levels of IgA enabling the efficient control of colitogenic bacteria and the prevention of the development of inflammatory disorders of the digestive system.

The dietary supplement of the present invention can however also be used for the therapy of inflammatory disorders of the digestive system, wherein a patient is regularly supplementing his diet with such a probiotic to modify his microbiome and strengthen the intestinal immune system. This may lead to a dampening and potentially termination of the pathological inflammatory reaction and a cure of the inflammatory disorder.

In a preferred embodiment, the composition for use as a medicament of the present invention comprises a filtrate of a bacterial mixture and/or culture after filtration through a 0.45 µm filter. It is a particular advantage of the present invention that bacteria of the order Anaeroplasmatales are 0.2-0.5 µm in size and therefore smaller than most bacteria of the intestinal microbiota. By filtration through 0.45 µm filter, such as a polyethersulfone (PES) filter, the percentage or relative share of Anaeroplasmatales can be enriched in a bacterial mixture or culture, which has for example been generated from the feces of a subject to establish a mixture of fecal microbiota. As shown in the examples below, it is possible to enriched bacteria of the order Anaeroplasmatales about 50-fold in such a mixture. Furthermore, it is possible to deplete other, probably less advantageous or less beneficial bacteria from such a mixture, such as those that don't induce IgA and TGF-beta, for example Erysipelotrichaceae incertae sedis, Mucispirillium (Deferribacteres), *Roseburia* (Firmicutes), *Anaerostipes* (Firmicutes), and *Papillibacter* (Firmicutes).

It is particularly preferred that the composition of the present invention causes increased IgA production in the intestine or other component of the digestive tract compared to subjects who have not received administration of the composition.

As explained above, bacteria of the order Anaeroplasmatales that are comprised by the composition of the present invention can induce the production of gastrointestinal IgA. IgA-immunoglobulins control colitogenic bacteria and contribute to an anti-inflammatory milieu in the digestive system, which is beneficial for preventing or treating inflammatory disorders of the digestive system. It is therefore particularly advantageous that the composition of the present invention maintains or even enhances these features of Anaeroplasmatales.

To determine an increased IgA production, the production or level of IgA in the intestine of a subject that has received a composition of the present invention is compared to the level of IgA in subjects that did not receive the composition of the present invention. Alternatively, the production or level of IgA in a subject that has received a composition of the present invention can be compared to the average production or level of IgA as determined in a representative group of individuals that represents a relevant reference group for said subject, such as healthy individuals or individuals suffering from a disorder of the digestive system. If the level of IgA is higher than the average IgA concentration in the reference group, IgA is considered increased. Furthermore, an increased IgA level may be determined by comparing the intestinal IgA level in the same subject before and after administration of the composition of the present invention. In another preferred embodiment, the composition for use as a medicament of present invention causes increased TGF-beta production in the intestine or other component of the digestive tract compared to subjects who have not received administration of the composition. TGF-beta is a cytokine or mediator that induces an anti-inflammatory environment and induces class switching of B-cells to IgA-producing B-cells. These features are particularly beneficial for the treatment or prevention of inflammatory disorders of the digestive system.

As explained for IgA above, an increased production of TGF-beta may be determined by comparing the production of TGF-beta in a subject that has received a composition of the present invention to the average production of TGF-beta in a relevant and/or representative group of individuals, for example healthy individuals or individuals suffering from a disorder of the digestive system, who did not receive the composition of the present invention, or to the production of TGF-beta in the same subject before administration of the composition of the present invention.

All embodiments of the composition described as for use as a medicament in the treatment or prevention of an inflammatory disorder of the digestive system are herewith also disclosed in the context of a method for treating or preventing an inflammatory disorder of the digestive system in a subject.

BRIEF DESCRIPTION OF THE DRAWINGS

The invention is further described by the following figures. These are not intended to limit the scope of the invention, but represent preferred embodiments of aspects of the invention provided for greater illustration of the invention described herein.

DETAILED DESCRIPTION

Figure 1:
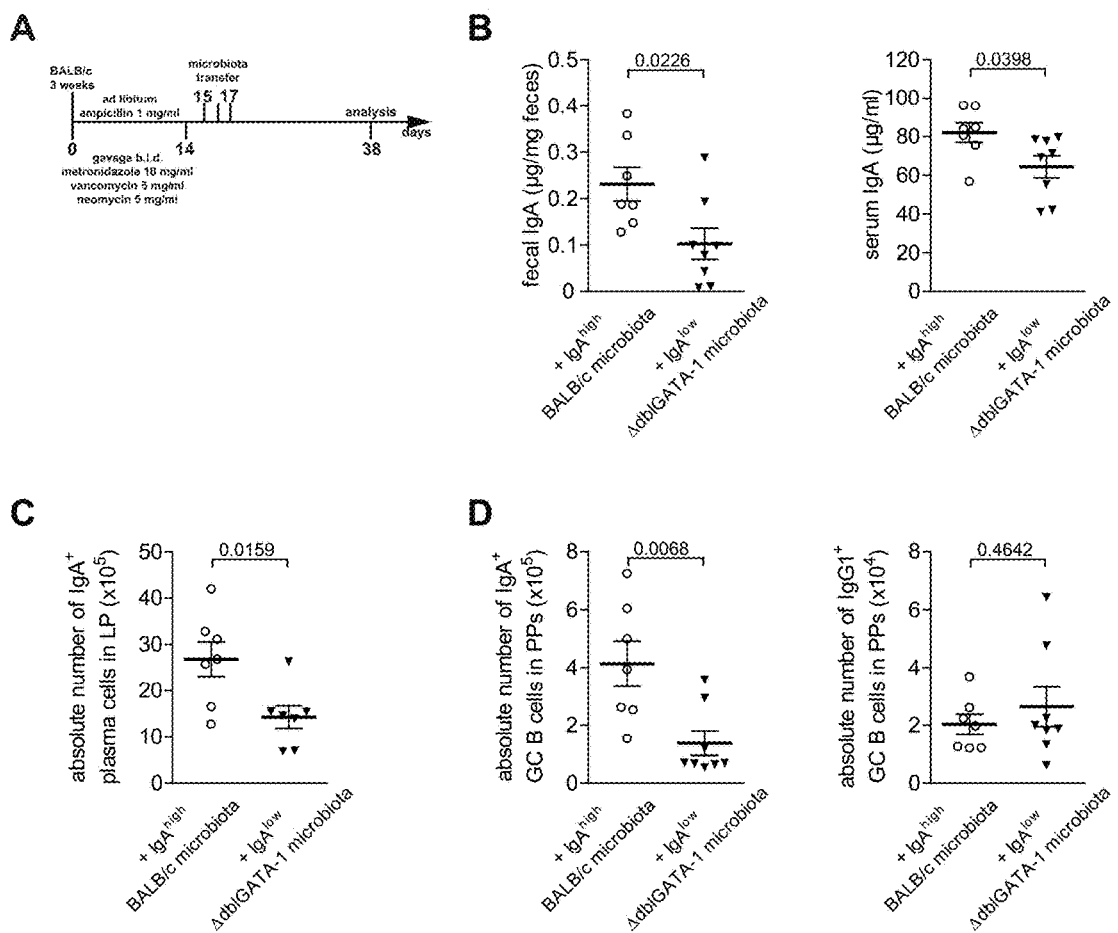
FIG. 1. Induction of mucosal IgA is dependent on the composition of the microbiota. (A) 6-week old BALB/c mice treated with an antibiotics cocktail (metronidazole 10 mg/ml, vancomycin 5 mg/ml, neomycin 5 mg/ml per gavage (200 μl) b.i.d. and ampicillin 1 mg/ml ad libitum via the drinking water) for 14 days were transferred with fecal microbiota from IgA$^{high}$ or IgA$^{low}$ mice on 3 consecutive days by gavage. Three weeks after microbiota transfer the mice were analysed. (B) IgA levels in feces and blood sera as measured by ELISA. (C and D) Flow cytometric determination of absolute numbers of CD45$^+$B220$^{lo}$ IgA$^+$siLP plasma cells (C) and B220$^+$PNA$^{hi}$IgA$^+$ and B220$^+$PNA$^{hi}$IgG1$^+$PP GC B cells (D). Error bars indicate SEM for n=8 mice from 2 independent experiments. p-values determined by unpaired two-tailed Student's t test.

Inflammatory diseases of the digestive system may be caused by a deregulation of the gastrointestinal immune system leading to an overreaction of inflammatory pathways, which may be due to a response to colitogenic bacteria. In this context, the present invention refers to a composition comprising one or more bacteria of the order Anaeroplasmatales for use as a medicament in the treatment or prevention of an inflammatory disorder of the digestive system. The term "bacteria" in the context of the present invention refers to a large domain of prokaryotic microorganisms. Bacteria display a wide diversity of morphologies and are typically 0.5-5.0 µm in length.

The bacterial phyla are the major lineages of bacteria, which are further subdivided into about 30 classes. Bacterial classes are subdivided into orders, which are constituted by bacterial families that comprise several genera, which finally comprise the bacterial species.

Tenericutes is a phylum of bacteria that contains the class Mollicutes. Notable genera include *Mycoplasma, Spiroplasma, Ureaplasma*, and *Phytoplasma*.

Mollicutes is a class of bacteria distinguished by the absence of a cell wall. Individual bacteria of the class are very small, typically only 0.2-0.3 µm (200-300 nm) in size and have a small genome. The best-known genus in the Mollicutes is *Mycoplasma*. Mollicutes are parasites of various animals and plants, living on or in the host's cells.

The class of Mollicutes comprises the order of Acholeplasmatales (comprising the family Acholeplasmataceae and the genus *Acholeplasma*), the order Anaeroplasmatales (comprising family Anaeroplasmataceae with genera *Anaeroplasma* and Asteroleplasma), the order Entomoplasmatales (comprising the family Entomoplasmataceae with the genera *Entomoplasma* and *Mesoplasma*, the family Spiroplasmataceae with the genus *Spiroplasma*), the order Haloplasmatales (comprising the family Haloplasmataceae and the genus *Haloplasma*) and the order Mycoplasmatales (comprising the family Mycoplasmataceae with the genera *Eperythrozoon, Haemobartonell, Mycoplasma* and *Ureaplasma*). This list is not meant to be exclusive, but lists non-limiting examples of orders, families and genera of the class of Mollicutes.

Anaeroplasmatales is an order of mollicute bacteria, which are generally found in the rumens of cattle and sheep, but also humans and mice. Members of the order Anaeroplasmatales can appear as different shapes at different times in their lifecycles. Cells, which are 16-18 hours old, tend to be spherical. When the cells are older, they can take on various shapes. Anaeroplasmatales cannot typically grow in the presence of oxygen. They do grow at a temperature of 37° C. on microbiological media, where they form irregular-shaped colonies with a "fried-egg" appearance, similar to other mycoplasmas. Anaeroplasmatales are negative by Gram stain. The order Anaeroplasmatales encompasses the family Anaeroplasmataceae, which encompasses the anaerobic mycoplasmas *Anaeroplasma* and Asteroleplasma.

In some embodiments, the inventive bacteria of the order Anaeroplasmatales may be classified or defined by functional effects, such as those functional effects demonstrated for the first time in the present invention. The inventive bacteria of the order Anaeroplasmatales may be classified or defined by one or more desired functions, selected from but not limited to the list of bacteria that induce production of IgA in the gastrointestinal system, do not induce an imbalance in the gastrointestinal immune system at the cost of other immunoglobulin-classes, but rather selectively strengthen immune responses that are mediated by IgA, induce TGF-beta in T follicular helper cells, induce T follicular helper cells in the PP to induce TGF-beta without modifying expression of other genes and especially immune-response modulating cytokines and/or induce the production of IgA irrespective of the specificity of the IgA producing B cells. Methods are available to persons skilled in the art to interrogate these properties without undue effort. For example, the present invention, including the examples demonstrated below, discloses multiple experimental approaches for objectively determining whether any given bacteria of the order Anaeroplasmatales exhibits the function characteristics described herein.

The examples of the present invention thereby present not only surprisingly beneficial properties of particular preferred bacteria for use in the present invention, but further enable the identification of relevant bacteria using the methodology described herein.

Furthermore, the diseases to be treated may be defined by the functional feature of an inflammatory disorder of the digestive system, that is associated with decreased levels of IgA in the gastrointestinal tract. For example, IgA levels can be measured by a skilled person using routine methods, which may be applied to any relevant medical condition (i.e. a sample obtained from a patient suffering from the condition or symptoms of the condition), in order to determine whether the medical agents of the present invention represent potentially effective means in treating said condition.

As used herein, "treatment" of or "treating" a subject afflicted with a disorder shall mean slowing, stopping or reversing the disorder's progression. In the preferred embodiment, treating a subject afflicted with a disorder means reversing the disorder's progression, ideally to the point of eliminating the disorder itself. As used herein, ameliorating a disorder and treating a disorder are equivalent. The treatment of the present invention may also, or alternatively, relate to a prophylactic administration of said composition. Such a prophylactic administration may relate to the "prevention" of any given medical disorder, or the prevention of development of said disorder, whereby prevention or prophylaxis is not to be construed narrowly under all conditions as absolute prevention. Prevention or prophylaxis may also relate to a reduction of the risk of a subject developing any given medical condition, preferably in a subject at risk of said condition.

The term "inflammatory disorder of the digestive system" relates to an inflammatory disease in which parts of the digestive system are affected by pathological inflammation. The digestive system comprises of the gastrointestinal tract plus accessory organs of digestion, such as the tongue, salivary glands, pancreas, liver, and gallbladder. The gastrointestinal tract comprises mouth, esophagus, stomach, the small intestine (further subdivided into the duodenum, jejunum and ileum) and large intestine (subdivided into the cecum, colon, rectum, and anal canal). Herein, digestive system and gastrointestinal tract as well as immune system of the digestive system and immune system of the gastrointestinal tract are used interchangeably.

As used herein the terms "inflammatory bowel disease", "inflammatory gastrointestinal disorder", and "inflammatory intestinal disease" may be considered as "inflammatory disorders of the digestive system". In some cases, these terms may be used interchangeably.

A preferred condition to be treated is inflammatory bowel disease. The term "inflammatory bowel disease" or "IBD" refers to a group of gastrointestinal disorders including, without limitation, Crohn's disease (CD), ulcerative colitis (UC), and indeterminate colitis (IC).

A preferred disease of the invention to be treated is therefore an inflammatory disease of the digestive or intestinal tract of said subject. Such diseases are characterized in that the disorder exhibits pathological inflammation that affects components of the digestive or intestinal tract of said subject. Such components of the digestive or intestinal tract may be any organ, tissue, cell or protein found in said area of the subject. The digestive or intestinal tract may be understood as the gastrointestinal tract (GI tract), which refers to the stomach and intestine, and is divided into the upper and lower gastrointestinal tracts, and may include all the structures from the mouth to the anus. The tract may also be divided into foregut, midgut, and hindgut, reflecting the embryological origin of each segment of the tract.

Crohn's disease (CD) is a disease of chronic inflammation that can involve any part of the gastrointestinal tract. Commonly, the distal portion of the small intestine, i.e., the ileum, and the cecum are affected. In other cases, the disease is confined to the small intestine, colon, or anorectal region. CD occasionally involves the duodenum and stomach, and more rarely the esophagus and oral cavity. The variable clinical manifestations of CD are, in part, a result of the varying anatomic localization of the disease. The most frequent symptoms of CD are abdominal pain, diarrhea, and recurrent fever. CD is commonly associated with intestinal obstruction or fistula, an abnormal passage between diseased loops of bowel. Crohn's disease, like many other chronic, inflammatory diseases, can cause a variety of systemic symptoms such as fevers and weight loss. Furthermore, Crohn's disease can affect many other organ systems and cause inflammation of the interior portion of the eye, known as uveitis, or inflammation of the white part of the eye (sclera), a condition called episcleritis. Crohn's disease may result in an increased risk for gallstones, which is due to a decrease in bile acid resorption in the ileum and the bile gets excreted in the stool, or in a type of rheumatologic disease known as seronegative spondyloarthropathy, which is characterized by inflammation of one or more joints (arthritis) or muscle insertions (enthesitis). Crohn's disease may also involve the skin, blood, and endocrine system resulting in manifestations such as erythema nodosum, pyoderma gangrenosum, increased risk of blood clots, deep venous thrombosis, autoimmune hemolytic anemia. Additionally, Crohn's disease may cause anemia with the associated symptoms of fatigue, a pale appearance, and other symptoms common in anemia. Crohn's disease can also cause neurological complications the most common of these are seizures, stroke, myopathy, peripheral neuropathy, headache and depression.

Ulcerative colitis (UC) is a disease of the large intestine characterized by chronic diarrhea with cramping, abdominal pain, rectal bleeding, and loose discharges of blood, pus, and mucus. The manifestations of UC vary widely. A pattern of exacerbations and remissions typifies the clinical course for about 70% of UC patients, although continuous symptoms without remission are present in some patients with UC. Local and systemic complications of UC include arthritis, eye inflammation such as uveitis, skin ulcers, and liver disease. In addition, UC, and especially the long-standing, extensive form of the disease are associated with an increased risk of colon carcinoma.

Colitis is an inflammation of the colon. Colitis may be acute and self-limited or long-term. It broadly fits into the category of digestive diseases. Symptoms of colitis may include: mild to severe abdominal pain and tenderness (depending on the stage of the disease), recurring bloody diarrhea with/without pus in the stools, fecal incontinence, flatulence, fatigue, loss of appetite and unexplained weight loss. In a medical context, the label colitis (without qualification) is used if: The cause of the inflammation in the colon is undetermined; for example, colitis may be applied to Crohn's disease at a time when the diagnosis is unknown, or the context is clear; for example, an individual with ulcerative colitis is talking about their disease with a physician who knows the diagnosis.

The terms "individual," "subject," or "patient" typically refer to humans, but also to other animals including, e.g., other primates, rodents, canines, felines, equines, ovines, porcines, mice and the like.

The present invention encompasses administration of the composition of the present invention to a subject. As used herein, "administration" or "administering" shall include, without limitation, introducing the composition by oral administration. Such administering can also be performed, for example, once, a plurality of times, and/or over one or more extended periods. A single administration is preferred, but repeated administrations over time (e.g., hourly, daily, weekly, monthly, quarterly, half-yearly or yearly) may be necessary in some instances. Such administering is also preferably performed using an admixture and a pharmaceutically acceptable carrier. Pharmaceutically acceptable carriers are well known to those skilled in the art.

Administration may also occur locally, for example by injection into the digestive system, for example by endoscopic or microinvasive means. Furthermore, bacteria of the composition of the present invention have been shown to migrate towards organs of the digestive system. Regardless, the oral as well as the local administration of the composition as described herein may lead to high levels of the cells at their site of action.

The composition described herein may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

Additionally, such compositions can comprise pharmaceutically acceptable carriers that can be aqueous or non-aqueous solutions, suspensions, and emulsions, most preferably aqueous solutions or solid formulations of various types known in the art. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as Ringer's dextrose, those based on Ringer's dextrose, and the like. Fluids used commonly for i.v. administration are found, for example, in Remington: The Science and Practice of Pharmacy, 20th Ed., p. 808, Lippincott Williams S-Wilkins (2000). Preservatives and other additives may also be present, such as, for example, antimicrobials, antioxidants, chelating agents, inert gases, and the like.

The term "intestinal microbiota" or "microbiota" relates to commensal, symbiotic and pathogenic microorganisms found in and on all multicellular organisms studied to date from plants to animals. Microbiota includes bacteria, archaea, protists, fungi and viruses. Microbiota have been found to be crucial for immunologic, hormonal and metabolic homeostasis of their host. The term microbiome describes the collective genomes of the microorganisms that reside in an environmental niche, such as in the digestive system of a subject. The symbiotic relationship between a host and its microbiota shapes the immune system of mammalians, insects, plants and aquatic organisms. In many animals including humans and mammals in general, the immune system and microbiota engage in "cross-talk", exchanging chemical or biochemical signals. This allows the immune system to recognize the types of bacteria that are harmful to the host and combat them, while allowing the helpful bacteria to carry out their functions; in turn, the microbiota influence immune reactivity and targeting. Bacteria can be transferred from mother to child through direct contact and after birth, or through indirect contact through eggs, coprophagy, and several other pathways. As the infant microbiome is established, commensal bacteria quickly populate the gut, prompting a range of immune responses and "programming" the immune system with long-lasting effects. The bacteria are able to stimulate lymphoid tissue associated with the gut mucosa, which enables the tissue to produce antibodies for pathogens that may enter the gut. The microbiome can be studied by analysis methods such as Targeted amplicon sequencing, metagenomics sequencing, and RNA and protein-based approaches. A bacterial operational taxonomic unit (OTU) is an operational definition used to classify groups of closely related bacteria. The term "bacterial OTU" is refers to clusters of bacteria, grouped by DNA sequence similarity of a specific taxonomic marker gene. In other words, OTUs are pragmatic proxies for microbial/bacterial "species" at different taxonomic levels, in the absence of traditional systems of biological classification. OTUs have become the most commonly used units of microbial diversity, especially when analyzing small subunit 16S or 18S rRNA marker gene sequence datasets. Sequences can be clustered according to their similarity to one another, and operational taxonomic units are defined based on the similarity threshold set by the researcher. Typically, OTUs are based on similar 16S rRNA sequences.

In the context of the present invention the term "colitogenic bacteria" relates to bacteria that may produce colitis and various forms of IBD. In inflammatory bowel disease (IBD), which includes Crohn's disease and ulcerative colitis, it is believed that the intestinal microbiota plays a key role in driving inflammatory responses during disease development and progression. As a result of microbial symbiosis and immunity, alterations in enteral bacteria may contribute to inflammatory diseases of the digestive system, such as IBD. IBD-affected individuals have been found to have 30-50 percent reduced biodiversity of commensal bacteria. Further evidence of the role of gut flora in the cause of inflammatory bowel disease is that IBD-affected individuals are more likely to have been prescribed antibiotics in the 2-5 year period before their diagnosis than unaffected individuals. The enteral bacteria can be altered by environmental factors, such as concentrated milk fats (a common ingredient of processed foods and confectionery) or oral medications such as antibiotics and oral iron preparations. The role of microbiota in the development of inflammatory diseases of the digestive system is further illustrated in mouse models of IBD, where the effects of the composition of the intestinal microbiota on disease have been examined. It has been revealed that particular bacterial taxa within the intestinal microbiota can be uniquely potent drivers of intestinal disease. For example, Prevotellaceae species drive chronic intestinal inflammation in mice with inflammasome-mediated dysbiosis and exacerbate chemically induced colitis and *Helicobacter* species can drive colitis in mice lacking the immunoregulatory cytokine interleukin-10. Thus, individual members of the intestinal microbiota vary dramatically in their propensity to induce inflammatory responses and, thereby, influence the development and progression of intestinal disease.

Preferably, the composition of the invention is prepared as a probiotic for oral administration suitable as a dietary supplement. In the context of the present invention, the term "probiotic" relates to live microorganisms that are administered to a subject to provide health benefits. Probiotics are microorganisms which are to be associated with health benefits in humans and animals after consumption or ingestions. Probiotics may be administered in the form of compositions, pharmaceutical compositions, in liquid or in solid form, or as dietary supplements, in yoghurts, food, beverages, or in other forms known to the skilled person. Studies have demonstrated effects of probiotics on intestinal inflammation, diarrhea, urogenital infections, allergies, blood pressure control, bacterial vaginosis, eczema, immune functions and infections, inflammation, IBD, lactose intolerance and urinary tract infections.

In the context of the invention, the term "dietary supplement" relates to components such as chemicals, microorganisms or biomolecules that are provided to a subject for oral administration potentially in conjunction with nutrients or food to provide a biologically beneficial effect to the subject. Dietary supplements as generally understood to include vitamins, minerals, fiber, fatty acids, probiotics or amino acids, among other substances. Sometimes dietary supplements are defined or categorized as foods, while in other cases they may be classified as drugs or other products.

Plasma cells, are also called plasma B cells, plasmocytes, plasmacytes, or effector B cells. Plasma cells are white blood cells/immune cells that secrete large volumes of antibodies. Plasma cells are transported by the blood plasma and the lymphatic system and originate in the bone marrow; B cells differentiate into plasma cells that produce antibody molecules. Once released into the blood and lymph, these antibody molecules bind to the target antigen (foreign substance) and initiate its neutralization or destruction by means of the immune system. B cells can differentiate into memory B cells or plasma cells upon stimulation, mostly by T cells, which usually occurs in germinal centers of secondary lymphoid organs like the spleen and lymph nodes. Germinal centers or germinal centres (GCs) are sites within secondary lymphoid organs where mature B cells proliferate, differentiate, and undergo somatic hypermutation and affinity maturation, and switch the class of their antibodies (for example from IgM to IgA during a normal immune response to an infection. They develop dynamically after the activation of follicular B cells by T-dependent antigen. Most of these B cells will become plasmablasts (or "immature plasma cells"), and eventually plasma cells, and begin producing large volumes of antibodies, while some B cells will undergo affinity maturation, which refers to the selection of antibodies with higher affinity for the antigen and the activation and growth of B cell clones able to secrete antibodies of higher affinity.

Class switching, also known as isotype switching, isotypic commutation or class-switch recombination (CSR), is a biological mechanism that changes a B cell's production of immunoglobulin (antibodies) from one type to another, such as from the isotype IgM to the isotype IgA. During this process, the constant-region portion of the antibody heavy chain is changed, but the variable region of the heavy chain stays the same (the terms "variable" and "constant" refer to changes or lack thereof between antibodies that target different epitopes). Since the variable region does not change, class switching does not affect antigen specificity. Instead, the antibody retains affinity for the same antigens, but can interact with different effector molecules.

T follicular helper cells or follicular B helper T cells (also known as TFH), are antigen-experienced CD4+ T cells found in the periphery within B cell follicles of secondary lymphoid organs such as lymph nodes, spleens and Peyer's patches, and are identified by their constitutive expression of the B cell follicle homing receptor CXCR5. Upon cellular interaction and cross signaling with their cognate follicular B cells, TFH cells trigger the formation and maintenance of germinal centers through the expression of CD40 ligand (CD40L) and the secretion of IL-21 and IL-4. TFH cells play a critical role in mediating the selection and survival of B cells that go on to differentiate either into special plasma cells capable of producing high affinity antibodies against foreign antigen, or memory B cells capable of quick immune re-activation in the future if ever the same antigen is re-encountered. TFH cells are also thought to facilitate negative selection of potentially autoimmune-causing mutated B cells in the germinal center and are involved in mediating Ig-class switching.

Peyer's patches, which are sometimes called aggregated lymphoid nodules, are organized lymphoid follicles, and are an important part of gut associated lymphoid tissue usually found in in the lowest portion of the small intestine, mainly in the distal jejunum and the ileum, but also could be detected in the duodenum. Peyer's patches are important for immune surveillance of the intestinal lumen and facilitate the generation of the immune response within the mucosa. Pathogenic microorganisms and other antigens entering the intestinal tract encounter macrophages, dendritic cells, B-lymphocytes, and T-lymphocytes found in Peyer's patches and other sites of gut-associated lymphoid tissue (GALT). Peyer's patches are covered by a special follicle-associated epithelium that contains so-called M cells, which sample antigen directly from the lumen and deliver it to antigen-presenting cells. However, dendritic cells and macrophages can also directly sample the lumen by extending dendrites through transcellular M cell-specific pores. T cells, B-cells and memory cells in the PP are stimulated upon encountering. These cells then pass to the mesenteric lymph nodes where the immune response is amplified. Activated lymphocytes pass into the blood stream via the thoracic duct and travel to the gut where they carry out their final effector functions. The maturation of B-lymphocytes takes place in the Peyer's patch.

Immunoglobulin A (IgA, also referred to as sIgA) is an antibody class that is crucial in the immune function of mucous membranes, for example in the digestive system. IgA has two subclasses (IgA1 and IgA2) and can be produced as a monomeric and as a dimeric form, wherein the dimeric form is the most prevalent and is also called secretory IgA (sIgA). sIgA is the main immunoglobulin found in mucous secretions, including tears, saliva, sweat, colostrum and secretions from the genitourinary tract, gastrointestinal tract, prostate and respiratory epithelium. Secretory IgA serves as the first line of defense in protecting the intestinal epithelium from enteric toxins and pathogenic microorganisms. Through a process known as immune exclusion, SIgA promotes the clearance of antigens and pathogenic microorganisms from the intestinal lumen by blocking their access to epithelial receptors, entrapping them in mucus, and facilitating their removal by peristaltic and mucociliary activities. In addition, SIgA functions in mucosal immunity and intestinal homeostasis, as SIgA influences the composition of the intestinal microbiota, down regulates proinflammatory responses normally associated with the uptake of highly pathogenic bacteria and potentially allergenic antigens, and promotes the retro-transport of antigens across the intestinal epithelium to DC subsets in GALTs. Cytokines are a diverse group of non-antibody proteins that act as mediators between cells. Cytokines are currently being clinically used as biological response modifiers for the treatment of various disorders. The term cytokine is a general term used to describe a large group of proteins. Particular kinds of cytokines may include Monokines, namely cytokines produced by mononuclear phagocytic cells, Lymphokines, namely cytokines produced by activated lymphocytes, especially Th cells, Interleukins, namely cytokines that act as mediators between leukocytes and Chemokines, namely small cytokines primarily responsible for leucocyte migration. Cytokine signaling is flexible and can induce both protective and damaging responses. They can produce cascades, or enhance or suppress production of other cytokines. Despite the various roles of cytokines, a skilled person is aware of which cytokines may be considered as immune response stimulating and therefore applied in the treatment of a tumor disease as described herein.

Transforming growth factor β or TGF-beta is a cytokine that exists in three known subtypes in humans, TGF-beta1, TGF-beta2, and TGF-beta3 play crucial roles in tissue regeneration, cell differentiation, embryonic development, and regulation of the immune system. Isoforms of transforming growth factor-beta (TGF-beta1) are also thought to be involved in the pathogenesis of pre-eclampsia. TGF-beta receptors are single pass serine/threonine kinase receptors. Furthermore, it has been found that TGF-beta1 induces IgA class switching of B cells and that an increase in TGF-beta1 leads to increased production of IgA.

EXAMPLES

The invention is further described by the following examples. These are not intended to limit the scope of the invention, but represent preferred embodiments of aspects of the invention provided for greater illustration of the invention described herein.

Materials and Methods of the Examples

Mice

IgA$^{high}$ BALB/c mice were purchased from Charles River Laboratories, Sulzfeld, Germany. IgA$^{low}$ BALB/c$^{\Delta dbIGATA-1}$ mice (16) were bred under specific pathogen-free conditions at the Bundesinstitut für Risikobewertung, Berlin.

Cohousing and Microbiota Transplantation

For cohousing experiments, BALB/c and BALB/c$^{\Delta dbIGATA-1}$ females were kept in the same cage at a ratio of 1:1 for three weeks. For the depletion of the native intestinal microbiota, BALB/c mice were treated with ampicillin (1 mg/ml ad libitum) via the drinking water and with additional gavage feedings b.i.d. of an antibiotics cocktail (neomycin 5 mg/ml, metronidazole 10 mg/ml and vancomycin 5 mg/ml, all purchased from Sigma, Darmstadt) for 14 days. Twenty-four hours after the last antibiotics administration the corresponding fecal microbiota was transferred via gavage on 3 consecutive days. For this, fresh fecal pellets of BALB/c (IgA$^{high}$) or BALB/c$^{\Delta dbIGATA-1}$ (IgA$^{low}$) mice were collected and resuspended in PBS (1 pellet in 1 ml). Following filtration through a 30 μm cell strainer (Partec, Görlitz), 200 μl of the suspension were transferred via gavage feeding.

The mice were analyzed three weeks after the last microbiota administration. All experiments were approved by the regulatory office "Landesamt für Gesundheit und Soziales" in Berlin, Germany. Determination of soluble IgA levels. Fresh feces were collected, weighed and resuspended in corresponding volume of PBS. The levels of fecal IgA in supernatants as well as in blood sera were determined by ELISA (Southern Biotech via BIOZOL Diagnostica, Eching).

Cell Isolation

For the isolation of LP cells, PP were removed and small intestines were longitudinally opened and washed in cold PBS. After cutting into short pieces, intestines were incubated twice in RPMI 1640 medium containing 25 mM EDTA, 10% FCS, 100 U/ml penicillin and 100 μg/ml streptomycin (P/S) for 15 min at 37° C. followed by vigorous shaking to remove the epithelium. Intestinal pieces were washed in PBS, homogenized using scalpel and digested twice with RPMI 1640 containing 10% FCS, 1 mg/ml Collagenase D (Roche, Mannheim), 0.1 mg/ml Dnase I (Sigma, Darmstadt) and 1 mg/ml Dispase II (Sigma, Darmstadt) for 20 min at 37° C. in a shaker at 200 rpm. Cell suspensions were passed through an 18 gauge needle and filtered through a 70 μm cell strainer (BD Biosciences, Heidelberg). After washing with RPMI 1640, 10% FCS, P/S cells were purified by 30% Percoll (GE Healthcare, Hamburg) solution in RPMI 1640, 10% FCS, P/S. Cells were then washed and resuspended in RPMI 1640, 10% FCS, P/S medium. To isolate cells from PP, tissue was removed from the small intestine, passed through a 70 μm cell strainer (BD Biosciences, Heidelberg) and resuspended in RPMI 1640, 10% FCS medium.

Flow Cytometry

Surface and intracellular staining was performed using following antibodies: IgG1-PE (RMG1-1), CXCR5-Bio (L138D7), PD-1-APC (29F.1Al2) purchased from BioLegend, Fell. B220-PerCP (RA3.6B2), CD3-Bio (145-2C11), CD4-PB (GK1.5) were purified and conjugated at DRFZ. CD45-FITC (30-F11) was purchased from eBioscience (Frankfurt). PNA-Bio (Vector via) and IgA-DyLight 650 (polyclonal) were purchased from BIOZOL Diagnostica (Eching) and BIOMOL GmbH (Hamburg) respectively. The staining of intracellular antigens was performed using the FoxP3 staining kit (eBioscience). Stained cells were acquired with a BD Canto II and data were analyzed with FlowJo V10 software. Tfh cells were sorted by flow cytometry with a BD Aria cell sorter as CD3+CD4+CXCR5'" PD-1'" cells.

Gene-Expression Analysis

Total RNA was extracted using QIAzol Lysis Reagent (Qiagen, Hilden). The reverse transcription into the cDNA was performed with the Sensiscript RT kit (Qiagen). The expression of TGF-beta and IL-4 was measured by real-time PCR (95° C. 30 sec; 60° C. 30 sec, 72° C. 30 sec; 50 cycles) with the StepOnePlus (Applied Biosystems) using Maxima SYBR Green/ROX qPCR Master Mix from Thermo Scientific and the following primers: TGF-beta (Fw: 5'-CACAGCTCACGGCACCGGAGA-3', SEQ ID NO: 1; 5'-Rv: GCTGTACTGTGTGTCCAGGCTCC-3', SEQ ID NO: 2); IL-4 (Fw: 5'-CGAGGTCACAG-GAGAAGGGACGC-3', SEQ ID NO: 3; Rv: 5'"-CCGAAAGAGTCTCTGCAGCTCC-3', SEQ ID NO: 4).

Analysis of Fecal Bacterial DNA

Bacterial DNA was isolated from frozen murine fecal pellets using ZR Fecal DNA MiniPrep Kit (Zymo Research, Freiburg) according to the manufacturer's protocol. The relative amount of specific bacterial phyla was quantified using a real time PCR (95° C. 30 sec; 55° C. 30 sec, 72° C. 30 sec; 50 cycles) and phyla specific 16S rRNA primers (17). The total amount of Eubacteria (18) was used as an internal reference. The deep sequencing analysis was performed by Illumina MiSeq V3 (300 bp paired-end read) using Bacteria 16S (341 F-785R) amplicon as described previously (19) Combined reads were classified using "classifier.jar" from the Ribosomal Database Project (20) with a confidence cutoff of 50% and agglomerated at Genus level using RDPUtils [Quensen J. RDPutils: R Utilities for Processing RDPTool Output. R package version 1.2]. Frequencies of bacterial genera were estimated using the copy number adjusted output and total bacterial counts. Heatmaps represent confidentially classified bacterial genera, with frequencies above 0.01% in non-cohoused BALB/c and below in non-cohoused BALB/c$^{\Delta dbIGATA-1}$ mice.

Preparation of Microbiota Filtrates

Fresh feces from IgA$^{high}$ mice were collected and resuspended in ice-cold PBS. The fecal suspension was subsequently filtered through a 70 μm (Corning), 30 μm (Partec, Görlitz) cell strainer, 5 μm (Merck via Sigma, Darmstadt) and 0.45 μm (Sarstedt, Nümbrecht) bacterial syringe filters. After centrifugation the pellet was added to the microbiota suspension of IgA$^{low}$ mice. 200 µl of the final product were administered per mouse by gavage.

Microbiota Analysis by High-Resolution Flow Cytometry

Fresh feces from Rag$^{-/-}$ mice were collected, resuspended in ice-cold PBS, filtered through a 30 µm (Partec) cell strainer and washed three times with PBS. The cell number was normalized to app. 3×10$^8$ per sample by setting OD700=0.035. The samples were incubated with the fecal supernatant of IgA$^{high}$ and IgA$^{low}$ BALB/c mice, blocked and stained with the anti-mouse IgA antibody (BIOMOL GmbH). After washing the samples were resuspended in SybrGreen (Invitrogen) solution and acquired on BDInflux (BD).

Statistical Analysis

Unpaired two-tailed Student's t test was used for statistical analysis.

Results of the Examples

Induction of Mucosal IgA is Dependent on the Composition of the Microbiota.

Figure 2:
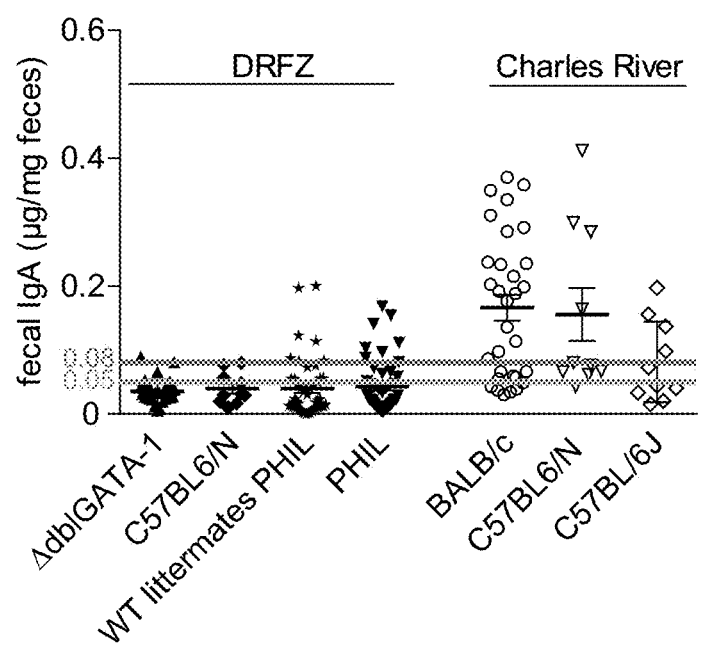
FIG. 2. Lower levels of fecal IgA in mice from DRFZ breeding facility than in mice from Charles River. IgA levels in the feces of different mouse strains bred in the DRFZ facility and at Charles River were measured by ELISA. Error bars indicate SEM of n=1046 mice.

Comparing the titers of fecal IgA of mice obtained from the DRFZ breeding facility to those obtained from Charles River Laboratories, Sulzfeld, Germany, mice from the DRFZ breeding facility had consistently lower titers of IgA. While feces of mice from the DRFZ breeding facility (IgA$^{low}$) had less than 0.05 µg IgA/mg feces, feces of Charles River mice (IgA$^{high}$) contained more than 0.08 µg IgA/mg feces (FIG. 2 and Table 1). This difference in IgA expression was dependent on the composition of the microbiota of the mice. Six-week old wild-type BALB/c mice from Charles River Laboratories (IgA$^{high}$; 0.166±0.020 µg IgA/mg feces) were treated for 2 weeks with a cocktail of antibiotics containing ampicillin, metronidazole, vancomycin, and neomycin, and subsequently transferred with the fecal microbiota of IgA$^{high}$ (BALB/c) and IgA$^{low}$ (BALB/c$^{\Delta dbIGATA-1}$; 0.035±0.003 µg IgA/mg feces) mice (FIG. 1A, FIG. 2 and Table 1). BALB/c$^{\Delta dbIGATA-1}$ mice have previously been described to have low IgA levels (10). Twenty-one days after transfer of the microbiota, mice that had received IgA$^{high}$ microbiota had significantly higher levels of IgA in feces (0.231±0.036 µg/mg feces) and sera (82.050±5.091 µg/ml), as compared to mice receiving the IgA$^{low}$ microbiota (fecal IgA: 0.103±0.034 µg/mg feces; serum IgA: 64.420±5.670 µg/ml) (FIG. 1B).

TABLE 1

Fecal IgA levels in Charles River and DRFZ mice.

| mouse strain | background | breeding facility | fecal IgA (µg/mg feces) mean ± SEM |
|---|---|---|---|
| C57BL/6N | C57BL/6 | Charles River | 0.155 ± 0.041 |
| BALB/c | BALB/c | Charles River | 0.166 ± 0.020 |
| C57BL/6J | C57BL/6 | Charles River | 0.081 ± 0.020 |
| ΔdblGATA-1 | BALB/c | DRFZ | 0.035 ± 0.003 |
| C57BL/6N | C57BL/6 | DRFZ | 0.040 ± 0.008 |
| PHIL | C57BL/6 | DRFZ | 0.043 ± 0.006 |
| WT PHIL littermates | C57BL/6 | DRFZ | 0.040 ± 0.007 |

Correspondingly, the absolute numbers of CD45$^+$IgA$^+$ B220$^{low}$ plasma cells in the small intestinal lamina propria (siLP) of IgA$^{high}$ microbiota recipients were about two-fold higher (26.83±3.75×10$^5$) than those of IgA$^{low}$ microbiota recipients (14.24±2.47×10$^5$) (FIG. 1C), and the absolute numbers of IgA+PNA$^{hi}$B220$^+$ germinal center (GC) B cells in the Peyer's patches (PP) of Ig microbiota recipients were about threefold increased (4.13±0.78×10$^3$), as compared to IgA$^{low}$ microbiota recipients (1.38±0.42×10$^3$) (FIG. 1D).

The impact of Ig microbiota was selective for IgA, since the absolute numbers of IgG1$^+$GC B cells in the PP were not significantly different between the mice of IgA$^{high}$ and IgA$^{low}$ recipient groups (2.03±0.35×10$^4$ versus 2.64±0.69×10$^4$) (FIG. 1D).

Cohousing with IgA$^{high}$ Mice Induces IgA in IgA$^{low}$ Mice.

Figure 3:
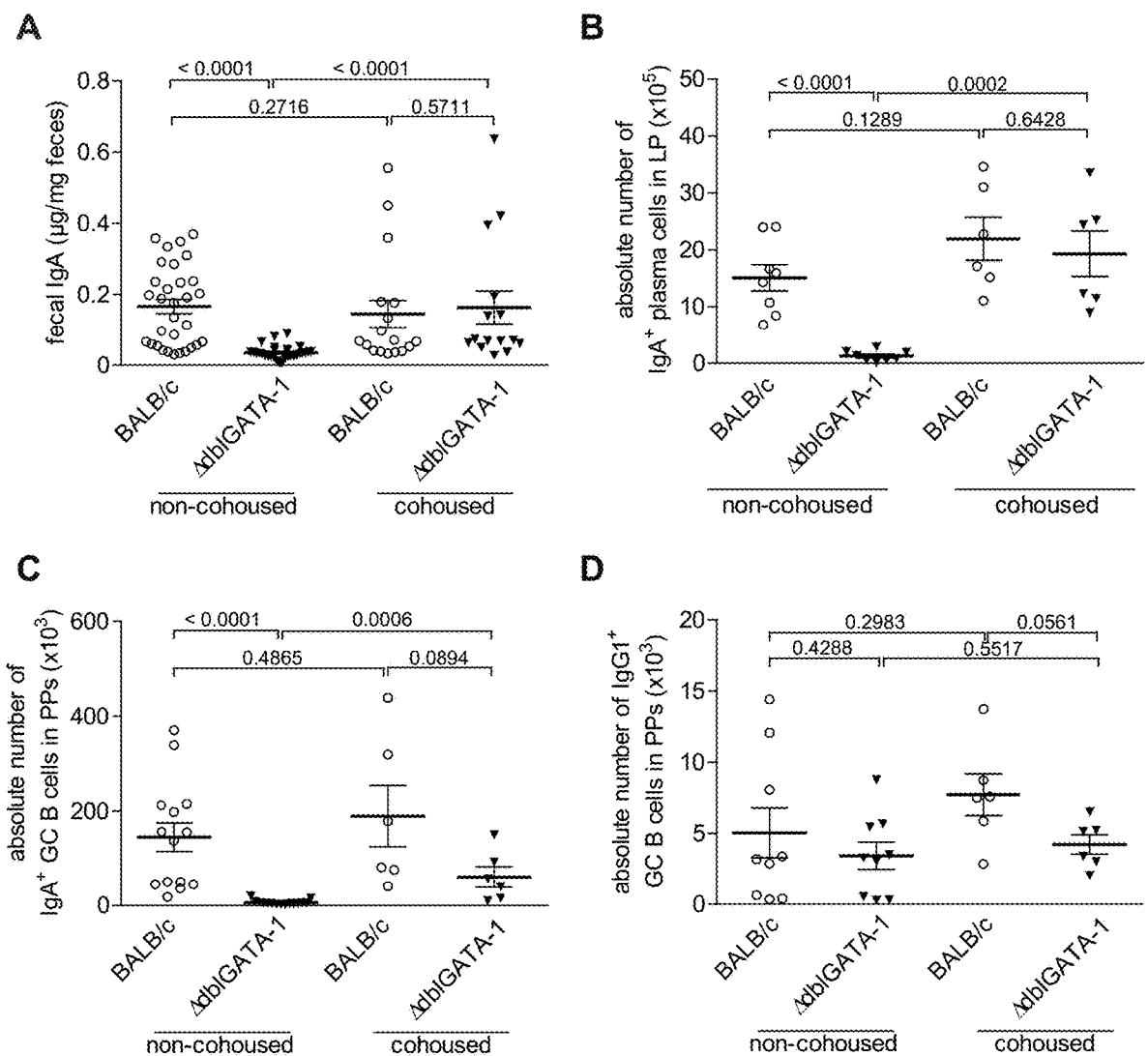
FIG. 3. Cohousing with IgA$^{high}$ mice induces IgA in IgA$^{low}$ mice. IgA$^{high}$ BALB/c and IgA$^{low}$ BALB/c$^{\Delta dbIGATA-1}$ mice were cohoused for 3 weeks. (A) IgA levels in feces of IgA$^{high}$ BALB/c and IgA$^{low}$ BALB/c$^{\Delta dbIGATA-1}$ mice under non-cohousing and cohousing conditions as measured. Panels (B), (C) and (D) show absolute numbers of IgA$^+$plasma cells in LP, IgA$^+$GCB cells in PPs and IgG1+GC B cells in PPs, respectively, in BALB/c mice, and IgA$^{low}$ BALB/c$\Delta$dbIGATA-1 mice, either non-cohoused or cohoused.

The effect of the microbiota on IgA expression was also observed in IgA$^{low}$ BALB/cΔdbIGATA-1 mice cohoused for 3 weeks with Ig BALB/c mice. In cohoused IgA$^{low}$ BALB/cΔdbIGATA-1 mice, the concentration of fecal IgA (0.163±0.046 µg/mg feces) was 4- to 5-fold higher than in non-cohoused IgA$^{low}$ BALB/c$^{\Delta dbIGATA-1}$ mice (0.035±0.003 µg/mg feces). Fecal IgA levels in cohoused and non-cohoused IgA$^{high}$ BALB/c mice were not different (0.145±0.039 µg/mg versus 0.166±0.020 µg/mg) (FIG. 3A and Table 1), indicating that the microbiota of IgA$^{high}$ mice, taken up by coprophagy by IgA$^{low}$ mice, induces IgA expression in the IgA$^{low}$ mice in a dominant fashion. Accordingly, both the absolute numbers of IgA$^+$plasma cells in the siLP of cohoused IgA$^{low}$ BALB/c$^{\Delta dbIGATA-1}$ mice increased from 1.28±0.34×10$^5$ to 19.32±4.00×10$^5$, similar to the number found in non-cohoused Ig BALB/c mice (15.11±2.30×10$^5$) (FIG. 3B). The absolute numbers of IgA+PNA$^{hi}$B220+GC B cells in the PP of cohoused IgA$^{low}$ BALB/cΔdbIGATA-1 mice increased 9-fold from 6.50±1.29×10$^3$ to 60.92±21.65×10$^3$, comparable to those of IgA$^{high}$ BALB/c mice (189.40±64.77×10$^3$) (FIG. 3C). The effect of cohousing was selective for IgA, since the absolute numbers of IgG1+PNA$^{hi}$B220+GC B cells in the PP of cohoused IgA$^{low}$ BALB/c$^{\Delta dbIGATA-1}$ mice (4.23±0.68×10$^3$) were comparable to those of non-cohoused IgA$^{high}$ BALB/c (5.05±1.75×10$^3$) and IgA$^{low}$ BALB/c$^{\Delta dbIGATA-1}$ mice (3.43±0.96×10$^3$) (FIG. 3D).

Induction of TGF-Beta Expressing T Follicular Helper Cells in Peyer's Patches

Figure 4:
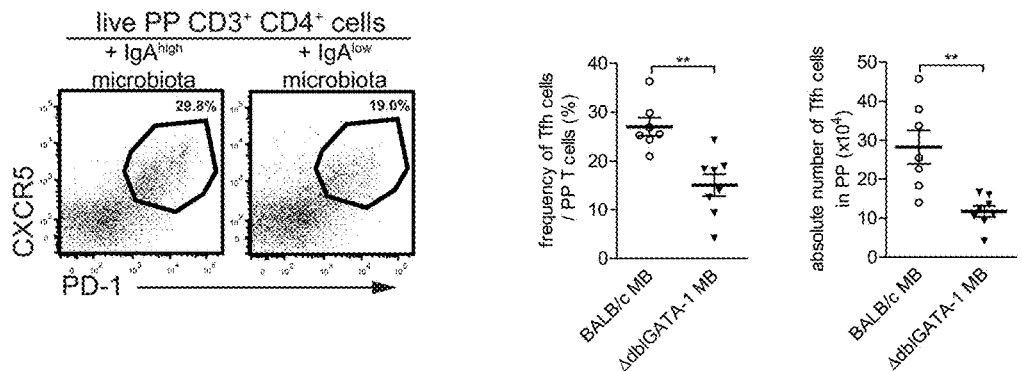
FIG. 4. Induction of TGF-beta expressing T follicular helper cells in Peyer's patches is determined by the composition of the intestinal microbiota. (A, B) Flow cytometric determination of frequencies and absolute numbers of CD3$^+$CD4$^+$CXCR5$^+$PD-1$^+$PP Tfh cells in BALB/c mice (A) treated with antibiotics and transferred with microbiota as described in FIG. 1 and (B) in non-cohoused and cohoused IgA$^{high}$ BALB/c and IgA$^{low}$ BALB/c$^{\Delta dbIGATA-1}$ mice. (C) Tgfb1 and (D) Il4 mRNA expression relative to Actb mRNA analysed by qRT-PCR in ex vivo isolated CD3$^+$CD4$^+$CXCR5$^+$PD-1$^+$PP Tfh cells from non-cohoused and cohoused IgA$^{high}$ BALB/c and IgA$^{low}$ BALB/c$^{\Delta dbIGATA-1}$ mice. Error bars indicate SEM for n=8-10 mice from 3 independent experiments. p-values determined by unpaired two-tailed Student's t test.
Figure 4:
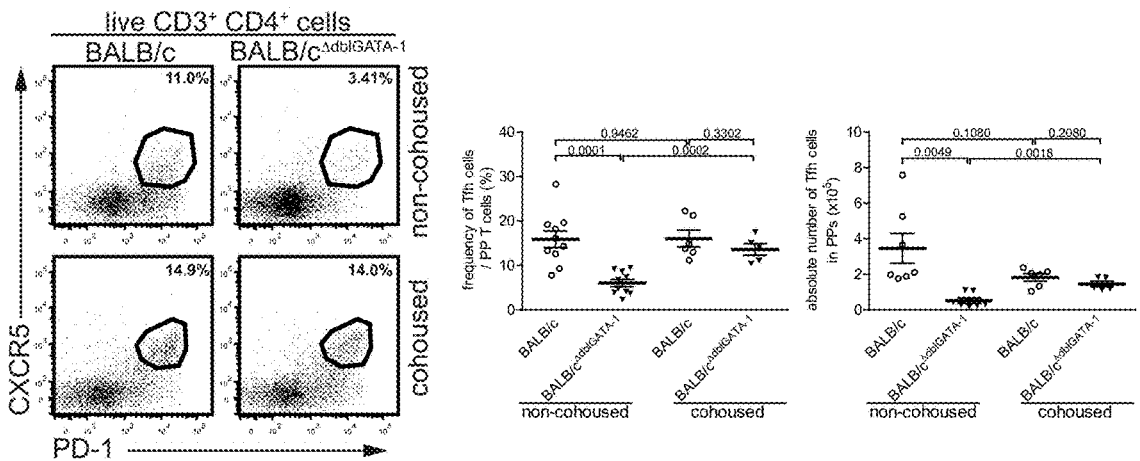
Figure 4:
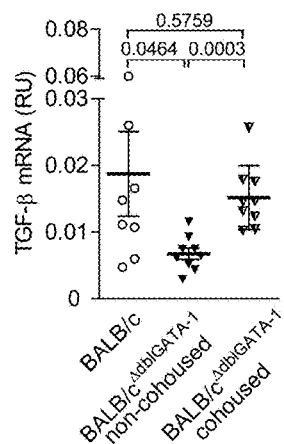
Figure 4:
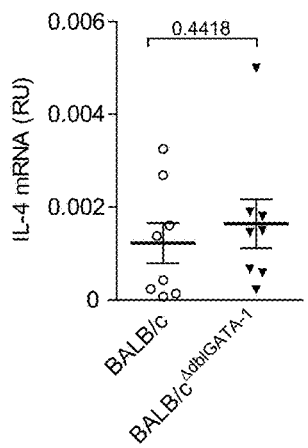

The selective and dominant effect of microbiota from IgA$^{high}$ mice on absolute numbers of IgA$^+$PNA$^{hi}$B220$^+$ germinal center (GC) B cells in the PP suggests that the microbiota influence antibody class switching directly. One possible mechanism for this is expression of the IgA-switch factor TGF-beta in Tfh cells (5, 6). Indeed, in BALB/c mice treated with antibiotics and gavaged with fecal microbiota of IgA$^{high}$ or IgA$^{low}$ mice (FIG. 1A), both the frequencies (27.03±1.84% versus 13.62±1.31%) and absolute numbers (28.26±4.28×10$^4$ versus 11.70±1.40×10$^4$) of CD3$^+$CD4$^+$CXCR5$^+$PD-1$^+$Tfh cells were higher in PP of IgA$^{high}$ microbiota recipients than in PP of IgA$^{low}$ microbiota recipients (FIG. 4A). Likewise, upon 3 weeks of cohousing of IgA$^{low}$ BALB/c$^{\Delta dbIGATA-1}$ mice with IgA$^{high}$ BALB/c mice, the frequencies (6.04±0.82% versus 13.62±1.31%) and the absolute numbers (0.52±0.15×10$^5$ versus 1.46±0.15×10$^5$) of PP Tfh cells in IgA$^{low}$ BALB/c$^{\Delta dbIGATA-1}$ mice had increased and resembled those of cohoused IgA$^{high}$ BALB/c mice (16.07±1.87% and 1.83±0.21×10$^5$) (FIG. 4B).

Figure 5:
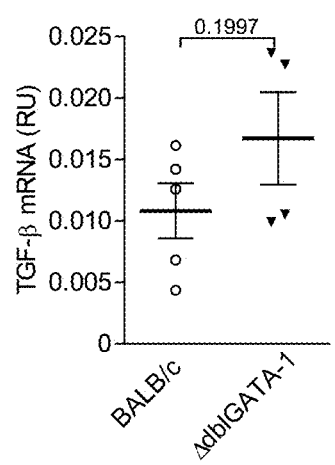
FIG. 5. Tgfb1 expression in MHCII$^+$ cells of the small intestinal lamina propria. Tgfb1 mRNA expression relative to Actb mRNA was analysed by qRT-PCR in ex vivo isolated CD4$^-$Siglec-F$^-$ MHCII$^+$ small intestinal lamina propria cells from IgA$^{high}$ BALB/c and IgA$^{low}$ BALB/c$^{\Delta dbIGATA-1}$ mice. Error bars indicate SEM of n=4-5 mice.

To examine the influence of fecal microbiota on Tfh cytokine expression, we isolated CD3$^+$CD4$^+$CXCR5$^+$PD-1$^+$ Tfh cells from PP of IgA$^{high}$ BALB/c mice, IgA$^{low}$ BALB/c$^{\Delta dbIGATA-1}$ mice, and of IgA$^{low}$ BALB/cΔdbIGATA-1 mice cohoused with IgA$^{high}$ BALB/c mice for 3 weeks, and measured Tgfb1 and Il4 expression, by quantitative RT-PCR directly ex vivo. PP Tfh cells of IgA$^{low}$ BALB/c$^{\Delta dbIGATA-1}$ mice showed a significantly lower expression of Tgfb1 than PP Tfh cells of IgA$^{high}$ BALB/c mice and those of IgA$^{low}$ BALB/c$^{\Delta dbIGATA-1}$ mice cohoused for 3 weeks with IgA$^{high}$ BALB/c mice (FIG. 4C). Il4 mRNA expression did not differ between Tfh of IgA$^{high}$ BALB/c and IgA$^{low}$ BALB/cΔdbIGATA-1 mice (FIG. 4D). TGF-beta production was affected selectively in Tfh cells, since in MHC class II-positive cells of the LP, Tgfb1 was not differentially expressed between the two mouse strains (FIG. 5), and in intestinal epithelial cells of IgA$^{high}$ BALB/c and IgA$^{1w}$ BALB/cΔdbIGATA-1 mice, Tgfb1 expression was not detectable (data not shown).

Anaeroplasma Induces Mucosal IgA

Figure 6:
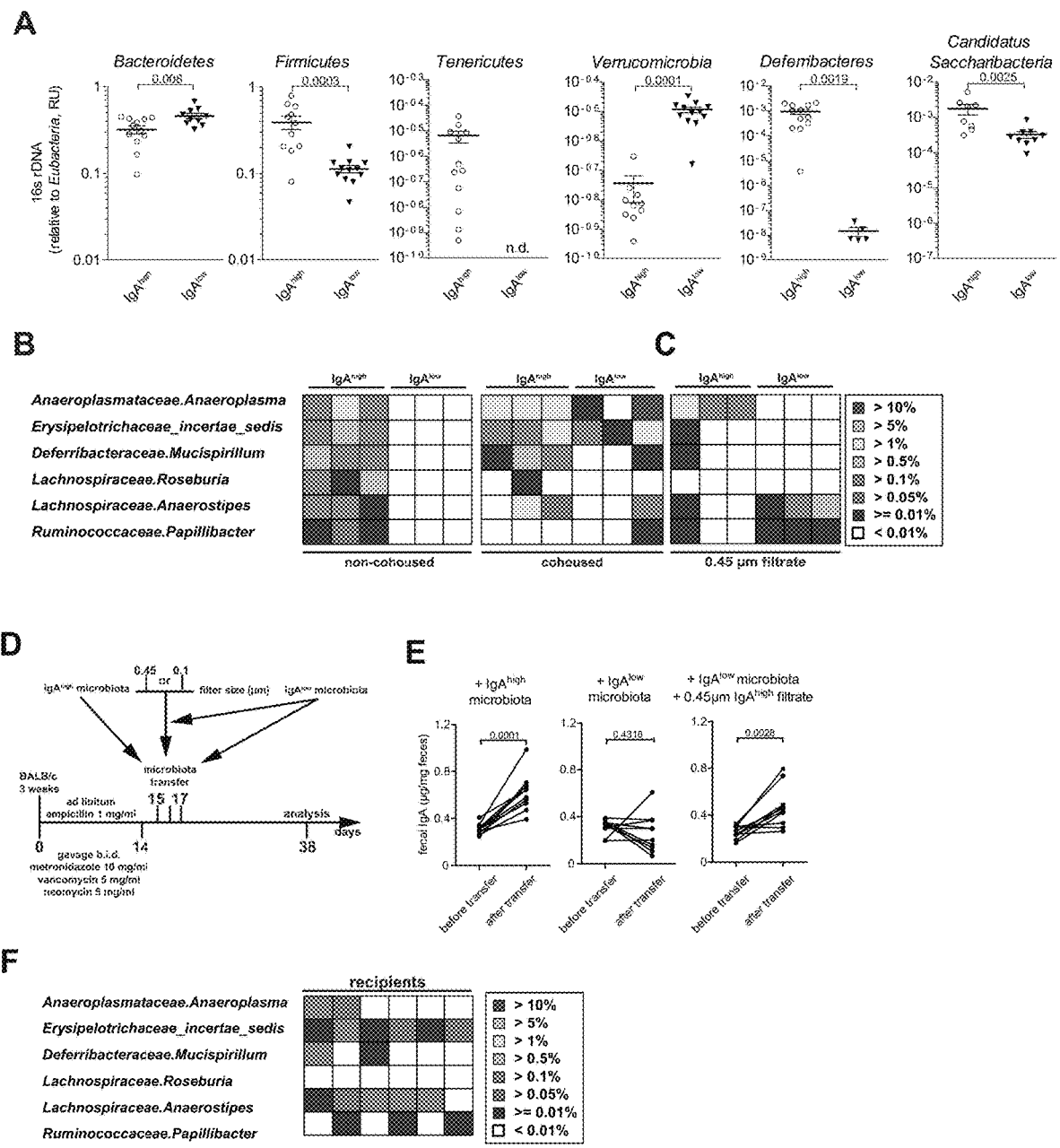
FIG. 6. *Anaeroplasma* induces mucosal IgA. (A) Relative amount of phyla specific 16S rDNA as measured by qRT-PCR for non-cohoused IgA$^{high}$ BALB/c and IgA$^{low}$ BALB/c$\Delta$dbIGATA-1 mice. Error bars indicate SEM for n=5-12 mice from 2 independent experiments. n.d.: not detectable. (B) Abundance of bacterial OTUs in the microbiota of non-cohoused IgA$^{high}$ BALB/c mice (frequencies above 0.01%) but not in IgA$^{low}$ BALB/c$^{\Delta dbIGATA-1}$ (frequencies below 0.01%) mice and their distribution following cohousing based on 16S rDNA deep sequencing. Heatmaps represent confidently classified genera. (C) Abundance of 6 previously defined bacterial OTUs in the 0.45 μm filtrate of IgA$^{high}$ BALB/c mice and IgA$^{low}$ BALB/c$^{\Delta dbIGATA-1}$ mice. Heatmaps represent confidently classified genera. (D) 3-week old BALB/c mice treated with antibiotics as described in FIG. 1 were transferred with IgA$^{high}$, IgA$^{low}$ or IgA$^{low}$ fecal microbiota supplemented with the 0.45 μm filtrate of IgA$^{high}$ microbiota on 3 consecutive days by gavage. (E) IgA levels in feces of microbiota recipients directly after antibiotics treatment and 3 weeks after microbiota transfer as determined by ELISA. n=10 mice from 2 independent experiments. (F) Abundance of 6 previously defined bacterial OTUs in the fecal microbiota of mice having received IgA$^{low}$ microbiota+0.45 μm IgA$^{high}$ filtrate or IgA$^{low}$ microbiota only recipients 3 weeks after microbiota transfer. p-values determined by unpaired two-tailed Student's t test.
Figure 7:
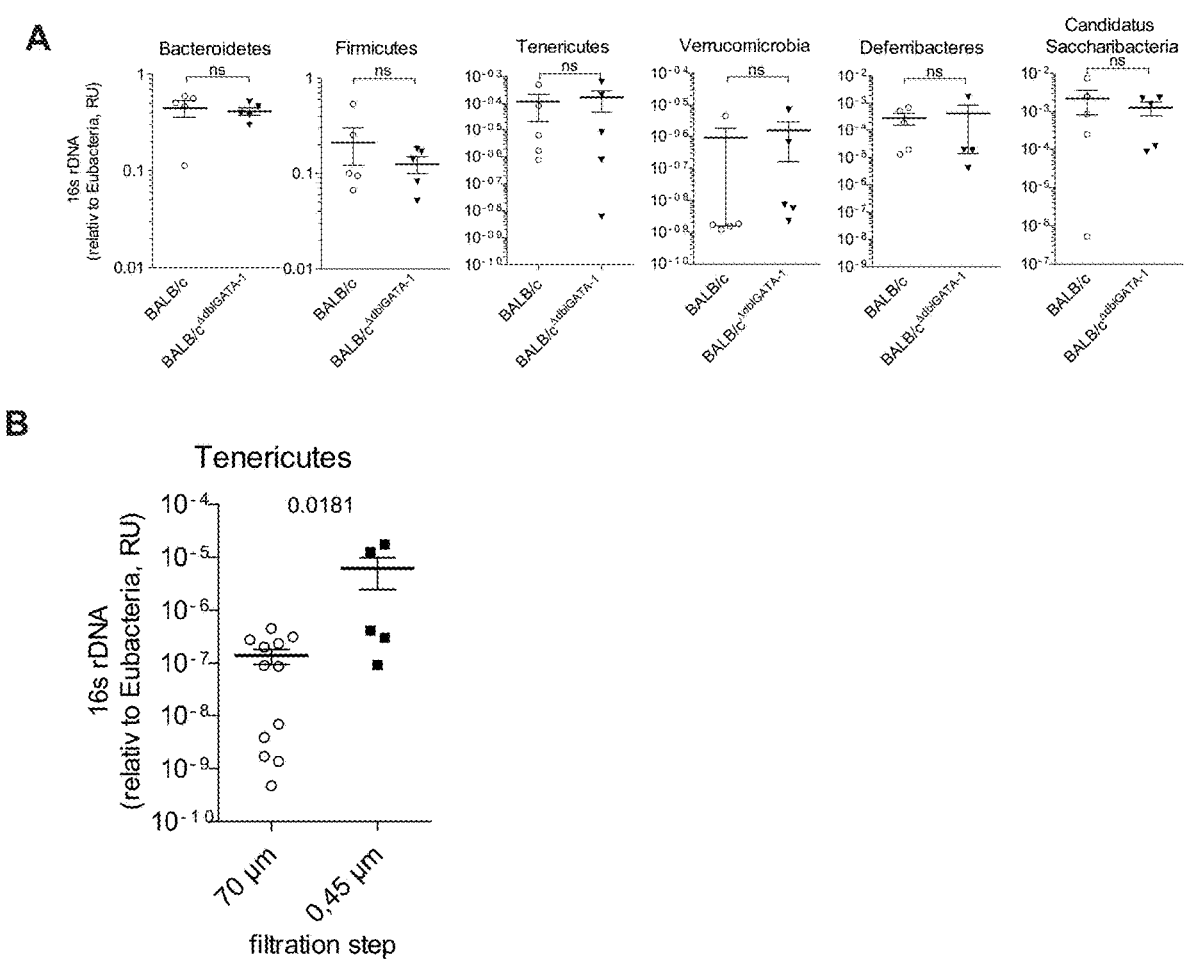
FIG. 7. Enrichment of Tenericutes from the total fecal microbiota by filtration. (A) Relative amount of bacterial phyla according to phyla specific 16S rDNA were quantified by qRT-PCR in the feces of cohoused IgA$^{high}$ BALB/c and IgA$^{low}$ BALB/c$^{\Delta dbIGATA-1}$ mice. Error bars indicate SEM of n=4-5 mice. p-values were determined by unpaired two-tailed Student's t test. (B) Relative abundance of Tenericutes following filtration of the fecal microbiota of IgA$^{high}$ BALB/c relative to total Eubacteria was measured by qRT-PCR. Feces from IgA$^{high}$ mice were collected and resuspended in PBS followed by subsequent filtration through 70 µm, 30 µm, 5 µm, 0.45 µm filters. Shown are the 70 µm and 0.45 µm flow-through. Error bars indicate SEM of n=5-12 mice. p-values were determined by unpaired two-tailed Student's t test.

To identify the bacteria responsible for the induction of IgA, the composition of the intestinal microbiota of IgA$^{low}$ and IgA$^{high}$ mice was compared by phylum-specific quantitative RT-PCR. Significant differences in the relative abundance of the phyla Bacteroidetes, Firmicutes, Tenericutes, Verrumicrobia, Defferibacteres, and Candidatus Saccharibacteria were evident (FIG. 6A), which disappeared following cohousing of IgA$^{low}$ mice and IgA$^{high}$ mice for 3 weeks (FIG. 7A). Sequencing of 16S rDNA from IgA$^{high}$ BALB/c mice and IgA$^{low}$ BALB/c$^{ΔdbIGATA-1}$ mice revealed that among the differentially represented bacterial operational taxonomic units (OTUs), 6 OTUs were present in the analyzed IgA$^{high}$ microbiota, and absent in the IgA$^{low}$ microbiota, but of those only 2 OTUs, Anaeroplasma (Tenericutes) and Erysipelotrichaceae incertae sedis (Firmicutes) were also detectable in 2 or 3 out of three IgA$^{low}$ mice after cohousing, thus qualifying as prime candidates for the induction of mucosal IgA (FIG. 6B). Tenericutes are 0.2-0.5 μm in size (11), smaller than most bacteria of the intestinal microbiota. By filtration through 0.45 μm polyethersulfone (PES) filters, Tenericutes of fecal microbiota were enriched about 50-fold (FIG. 7B) and depleted of Erysipelotrichaceae incertae sedis, but also of Mucispirillium (Deferribacteres), Roseburia (Firmicutes), Anaerostipes (Firmicutes), and Papillibacter (Firmicutes) (FIG. 6C), i.e. all those OTUs differentially present in IgA$^{high}$ versus IgA$^{low}$ mice. When comparing the bacterial composition of 0.45 μm filtrates of fecal microbiota of IgA$^{high}$ BALB/c mice and IgA$^{low}$ BALB/c$^{ΔdbIGATA-1}$ mice, all bacteria except Anaeroplasma were either present or absent in both filtrates (FIG. 6C).

Anaeroplasma was exclusively present in filtrate of IgA$^{high}$ BALB/c mice. This filtrate was then used to supplement IgA$^{low}$ microbiota and transfer it into antibiotics-treated IgA$^{high}$ BALB/c mice (FIG. 6D). Transfer of IgA$^{low}$ microbiota alone did not increase IgA expression (0.314±0.021 μg/mg feces before transfer versus 0.262±0.051 μg/ml feces after transfer). Transfer of IgA$^{low}$ microbiota supplemented with the 0.45 μm filtrate of IgA$^{high}$ microbiota induced fecal IgA levels from 0.255±0.017 μg/mg feces to 0.469±0.055 μg/mg feces, within 3 weeks, comparable to the transfer of the entire IgA$^{high}$ microbiota (from 0.307±0.014 μg/mg feces to 0.612±0.051 μg/mg feces) (FIG. 6E). Erysipelotrichaceae incertae sedis was detectable in the Ig BALB/c mice before and after treatment with antibiotics, thus excluding it as a candidate for induction of IgA (FIG. 6F). Anaeroplasma was detectable only in 2 out of 3 mice receiving the 0.45 μm filtrate of IgA$^{high}$ microbiota 3 weeks after transfer of the filtrate, and only these two mice had increased levels of IgA, confirming Anaeroplasma as the inducer of mucosal IgA (FIG. 6F).

Anaeroplasma Enhances Mucosal Immune Responses to IgA

Figure 8:
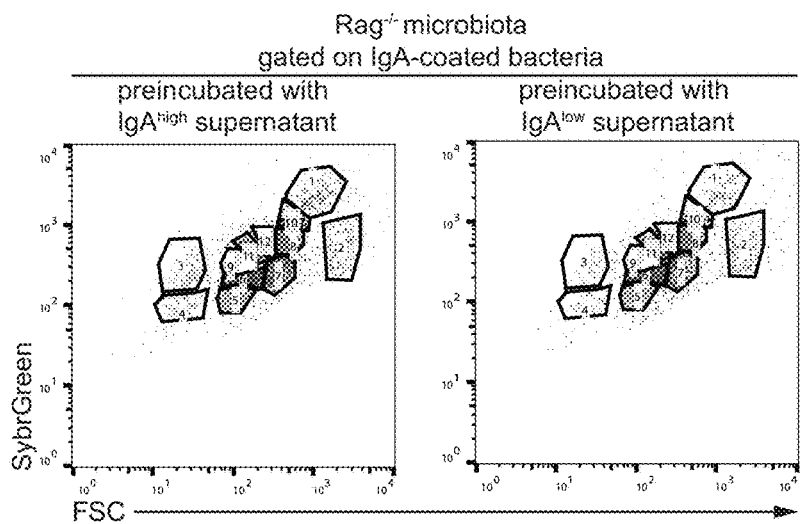
FIG. 8. *Anaeroplasma* enhances mucosal immune responses to IgA, irrespective of the specificity. The microbiota of Rag$^{-/-}$ mice was incubated with the undiluted fecal supernatant from IgA$^{high}$ or IgA$^{low}$ BALB/c mice (see FIG. 1A), stained with anti-mouse IgA antibody and the DNA dye SybrGreen and analyzed by high-resolution flow cytometry on a BDInflux. (A) For quantitative comparison of bacteria stained with fecal IgA of IgPO or IgA$^{low}$ mice we used the cytometric barcoding (flowCyBar) approach (21) in which a gate template composed of all gates occurring in either samples pre-gated on IgA$^+$ bacteria was generated. (B) Frequencies of bacteria in the indicated gates are shown. (C) Titration of fecal supernatant from IgA$^{high}$ or IgA$^{low}$ mice on Rag$^{-/-}$ derived fecal microbiota. Mean fluorescence intensity (MFI) for the IgA$^+$ population at the respective dilution is indicated.
Figure 8:
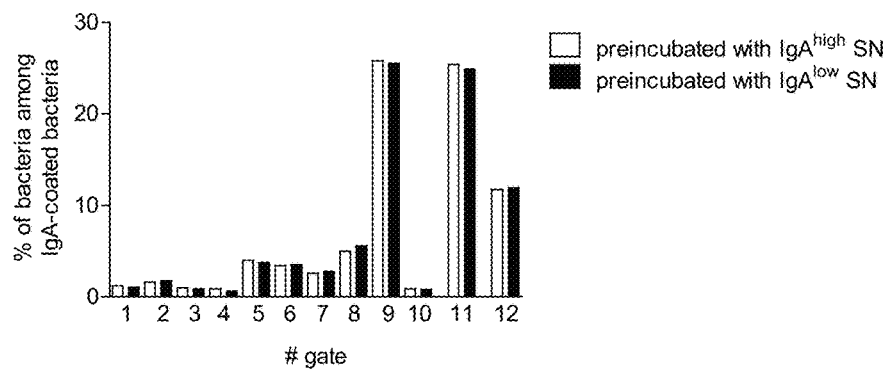
Figure 8:
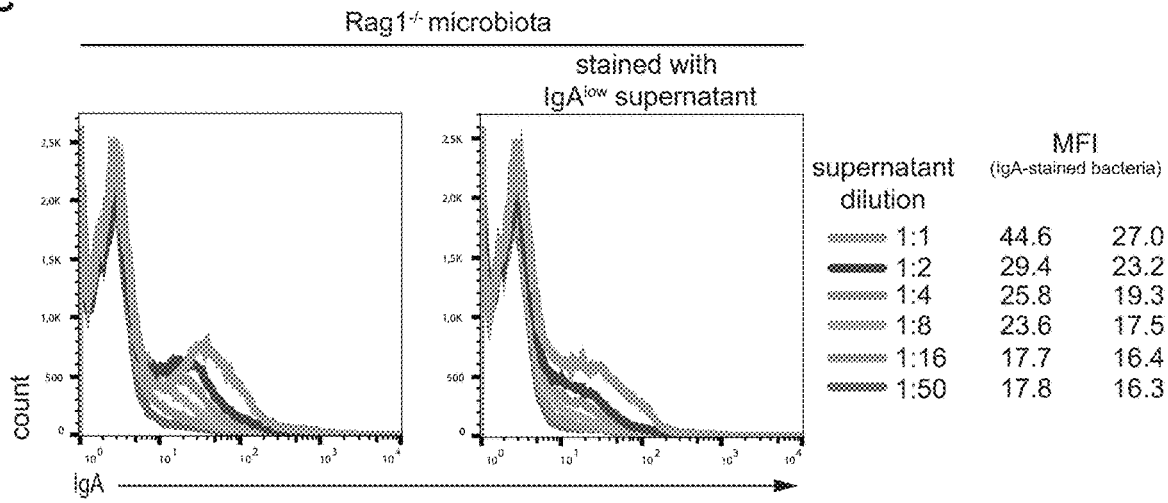
Figure 9:
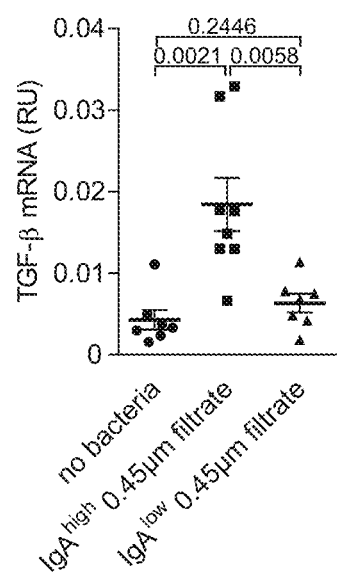
FIG. 9. IgA$^{high}$ 0.45 µm filtrate induces TGF-beta in splenocytes in vivo. Splenocytes of BALB/c mice were isolated and cultured on a-CD3 (3 µg/µl) and a-CD28 (3 µg/ml) coated plates. A 0.45 µm fecal filtrate from IgA$^{low}$ and IgA$^{high}$ mice was added to the culture at time point 0 h. After 48 h 50 ng/mo PMA and 5 µg/ml Ionomycin was added to the cells for 3 hours. RNA was isolated from the cells, cDNA was generated and TGF-beta mRNA was detected by qPCR.

Fecal IgA of IgA$^{high}$ mice and of IgA$^{low}$ mice was used to stain the fecal microbiota, containing Anaeroplasma (data not shown), of Rag-deficient mice. Comparative high-resolution flow cytometry of the microbiota (12) showed the same staining pattern for both (FIG. 8A). In each of the 12 gates shown in FIG. 8A, the frequencies of stained bacteria were the same, for IgA of IgA$^{high}$ and IgA$^{low}$ mice (FIG. 8B). Finally, titration of IgA of IgA$^{high}$ and IgA$^{low}$ mice on Rag$^{-/-}$ microbiota demonstrates an about 2-fold difference in mean fluorescence intensity (MFI) (FIG. 8C), confirming that Anaeroplasma itself does not target IgA responses to distinct bacteria, but rather directs IgA class switching as such.

DISCUSSION

Here we have identified for the first time a distinct member of microbiota which controls mucosal IgA and TGF-beta production. We show that bacteria of the genus Anaeroplasma induce mucosal IgA expression in a dominant fashion, by induction of mucosal Tfh cells expressing TGF-beta, the cytokine controlling class switch recombination to IgA. In contrast to the species-specific induction of IgA in mucosal immune reactions to colitogenic bacteria (1), Anaeroplasma controls IgA production as such, in a generic fashion. Anaeroplasma thus qualifies as a key anti-inflammatory component of the microbiota, since both, TGF-beta and IgA have been shown to protect from intestinal inflammation (13, 14). By dictating antibody class switching to IgA, Anaeroplasma controls mucosal immune reactions that have been shown to be directed against colitogenic bacteria (1).

At present it is not clear how Anaeroplasma induces transcription of the Tgfb1 gene in Tfh cells. It should be noted that Anaeroplasma, like all Tenericutes, does not have a cell wall (11) and thus escapes notice of inflammatory cell wall-detecting pattern recognition receptors. Despite its lack of a cell wall, Anaeroplasma is quite robust. It survives in feces and is transferred efficiently by coprophagy, as we show here. Anaeroplasma is a component of human microbiota (15), and thus qualifies as a probiotic therapy of intestinal inflammation.

REFERENCES

1. N. W. Palm et al., Immunoglobulin A coating identifies colitogenic bacteria in inflammatory bowel disease. Cell 158, 1000-1010 (2014).
2. P. A. Crabbe, H. Bazin, H. Eyssen, J. F. Heremans, The normal microbial flora as a major stimulus for proliferation of plasma cells synthesizing IgA in the gut. The germ-free intestinal tract. International archives of allergy and applied immunology 34, 362-375 (1968).
3. S. Hapfelmeier et al., Reversible microbial colonization of germ-free mice reveals the dynam-ics of IgA immune responses. Science 328, 1705-1709 (2010).
4. C. Lindner et al., Diversification of memory B cells drives the continuous adaptation of secretory antibodies to gut microbiota. Nat Immunol 16, 880-888 (2015).
5. M. Dullaers et al., A T cell-dependent mechanism for the induction of human mucosal hom-ing immunoglobulin A-secreting plasmablasts. Immunity 30, 120-129 (2009).
6. M. Tsuji et al., Preferential generation of follicular B helper T cells from Foxp3+ T cells in gut Peyer's patches. Science 323, 1488-1492 (2009).
7. K. B. Islam, L. Nilsson, P. Sideras, L. Hammarstrom, C. I. Smith, TGF-beta 1 induces germ-line transcripts of both IgA subclasses in human B lymphocytes. Int Immunol 3, 1099-1106 (1991).
8. P. Shockett, J. Stavnezer, Effect of cytokines on switching to IgA and alpha germline tran-scripts in the B lymphoma 1.29 mu. Transforming growth factor-beta activates transcription of the unrearranged C alpha gene. J Immunol 147, 4374-4383 (1991).

9. M. Lorenz, S. Jung, A. Radbruch, Switch transcripts in immunoglobulin class switching. Sci-ence 267, 1825-1828 (1995).
10. V. T. Chu et al., Eosinophils promote generation and maintenance of immunoglobulin-A-expressing plasma cells and contribute to gut immune homeostasis. Immunity 40, 582-693 (2014).
11. M. ROBINSON, M. J. ALLISON, P. A. HARTMAN, *Anaeroplasma* abactoclasticum gen.nov., sp.nov.: an Obligately Anaerobic *Mycoplasma* from the Rumen. International Jour-nal of Systematic and Evolutionary Microbiology 25, 173-181 (1975).
12. J. Zimmermann et al., High-resolution microbiota flow cytometry reveals dynamic coli-tis-associated changes in fecal bacterial composition. Eur J Immunol 46, 1300-1303 (2016).
13. M. O. Li, R. A. Flavell, Contextual regulation of inflammation: a duet by transforming growth factor-beta and interleukin-10. Immunity 28, 468-476 (2008).
14. C. Gutzeit, G. Magri, A. Cerutti, Intestinal IgA production and its role in host-microbe inter-action. Immunol Rev 260, 76-85 (2014).
15. C. Human Microbiome Project, Structure, function and diversity of the healthy human micro-biome. Nature 486, 207-214 (2012).
16. C. Yu et al., Targeted deletion of a high-affinity GATA-binding site in the GATA-1 promoter leads to selective loss of the eosinophil lineage in vivo. J Exp Med 195, 1387-1395 (2002).
17. Y. W. Yang et al., Use of 16S rRNA Gene-Targeted Group-Specific Primers for Real-Time PCR Analysis of Predominant Bacteria in Mouse Feces. Appl Environ Microbiol 81, 6749-6756 (2015).
18. N. H. Salzman et al., Enteric defensins are essential regulators of intestinal microbial ecolo-gy. Nat Immunol 11, 76-83 (2010).
19. J. Zimmermann et al., High-resolution microbiota flow cytometry reveals dynamic colitis-associated changes in fecal bacterial composition. Eur J Immunol 46, 1300-1303 (2016).
20. J. R. Cole et al., Ribosomal Database Project: data and tools for high throughput rRNA analy-sis. Nucleic Acids Res 42, D633-642 (2014).
21. C. Koch, S. Gunther, A. F. Desta, T. Hubschmann, S. Muller, Cytometric fingerprinting for analyzing microbial intracommunity structure variation and identifying sub-commu-nity function. Nat Protoc 8, 190-202 (2013)

---

What is claimed is:

1. A method for treating an inflammatory disorder of the digestive system in a subject, wherein the method comprises administering a composition comprising one or more bacteria of the order Anaeroplasmatales to the subject, thereby inducing production of IgA in the gastrointestinal system.

2. The method of claim 1, wherein the one or more bacteria of the order Anaeroplasmatales is/are *Anaeroplasma*.

3. The method of claim 1, wherein the inflammatory disorder of the digestive system is a colitis.

4. The method of claim 1, wherein the inflammatory disorder of the digestive system is associated with colitogenic bacteria.

5. The method of claim 1, wherein the inflammatory disorder of the digestive system is an inflammatory bowel disease.

6. The method of claim 5, wherein the inflammatory disorder of the digestive system is Crohn's disease (CD).

7. The method of claim 5, wherein the inflammatory disorder of the digestive system is ulcerative colitis (UC).

8. The method of claim 1, wherein the inflammatory disorder of the digestive system is associated with decreased levels of IgA in the gastrointestinal tract compared to a healthy individual.

9. The method of claim 1, wherein the composition is in a form suitable for oral administration.

10. The method of claim 1, wherein the composition is prepared as a probiotic for oral administration suitable as a dietary supplement.

11. The method of claim 1, wherein the composition comprises a filtrate of a bacterial mixture and/or culture after filtration through a 0.45 μm filter.

12. The method of claim 1, wherein the composition causes increased IgA production in the intestine or other component of the digestive tract compared to subjects who have not received administration of the composition.

13. The method of claim 1, wherein the composition causes increased TGF-beta production in the intestine or other component of the digestive tract compared to subjects who have not received administration of the composition.

14. The method of claim 1, wherein the subject has gastrointestinal microbiota that do not comprise bacteria of the order Anaeroplasmatales, thereby establishing bacteria of the order Anaeroplasmatales as part of the gastrointestinal microbiota of the subject.

* * * * *